United States Patent
Durante et al.

(10) Patent No.: US 8,986,315 B2
(45) Date of Patent: Mar. 24, 2015

(54) AIMING DEVICE HAVING RADIO-OPAQUE MARKERS

(75) Inventors: Oliviero Durante, Oberdorf (CH); Tom Overes, Oberdorf (CH); Bruno Walter, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 257 days.

(21) Appl. No.: 13/481,027

(22) Filed: May 25, 2012

(65) Prior Publication Data

US 2012/0303038 A1 Nov. 29, 2012

Related U.S. Application Data

(60) Provisional application No. 61/489,930, filed on May 25, 2011, provisional application No. 61/501,868, filed on Jun. 28, 2011.

(51) Int. Cl.
*A61B 17/90* (2006.01)
*A61B 17/17* (2006.01)
*A61B 19/00* (2006.01)

(52) U.S. Cl.
CPC .......... *A61B 17/1725* (2013.01); *A61B 17/1703* (2013.01); *A61B 19/54* (2013.01)
USPC .......................................................... 606/96

(58) Field of Classification Search
USPC .............. 600/587, 594; 606/86 R, 96–98, 99; 623/22.11–22.2
See application file for complete search history.

(56) References Cited

U.S. PATENT DOCUMENTS

| | | | |
|---|---|---|---|
| 2,519,003 A | 8/1950 | Stephens | |
| 4,865,025 A | 9/1989 | Buzzi et al. | |
| 5,433,720 A | 7/1995 | Faccioli et al. | |
| 5,628,750 A | 5/1997 | Whitlock et al. | |
| 6,258,096 B1 | 7/2001 | Seki | |
| 6,926,720 B2 | 8/2005 | Castaneda | |
| 7,481,815 B2 | 1/2009 | Fernandez | |
| 7,853,311 B1 * | 12/2010 | Webb | 600/426 |
| 2005/0131418 A1 | 6/2005 | Mor | |
| 2005/0177175 A1 | 8/2005 | Johnstone | |
| 2005/0261696 A1 | 11/2005 | Overes et al. | |
| 2006/0064106 A1 * | 3/2006 | Fernandez | 606/98 |

(Continued)

FOREIGN PATENT DOCUMENTS

| | | |
|---|---|---|
| EP | 0589592 | 3/1994 |
| JP | 2007/143492 | 6/2007 |

(Continued)

OTHER PUBLICATIONS

International Patent Application No. PCT/US2012/039571: International Search Report and Written Opinion dated Jul. 17, 2012, 15 pages.
International Patent Application No. PCT/US2012/039574: International Search Report and Written Opinion dated Jul. 17, 2012, 13 pages.

*Primary Examiner* — Christopher Beccia
(74) *Attorney, Agent, or Firm* — Baker & Hostetler LLP

(57) ABSTRACT

An aiming arm can include at least a pair of radiographic markers that define a first radiographic image characteristic when a radiographic image source is not adequately aligned with the aiming arm, and a second desired radiographic image characteristic when the radiographic image source is adequately aligned with the aiming arm. Once the radiographic image source has been aligned with the aiming arm, the position of the aiming arm relative to an underlying implant can be visually inspected to determine whether the aiming arm is aligned with the underlying implant.

19 Claims, 17 Drawing Sheets

(56) References Cited

U.S. PATENT DOCUMENTS

| | | |
|---|---|---|
| 2006/0106400 A1 | 5/2006 | Fernandez et al. |
| 2008/0058829 A1* | 3/2008 | Buscher et al. ........... 606/96 |
| 2009/0069816 A1 | 3/2009 | Sasing et al. |
| 2009/0088767 A1 | 4/2009 | Leyden et al. |
| 2009/0131951 A1 | 5/2009 | Fernandez |
| 2010/0152740 A1 | 6/2010 | O'Reilly et al. |

FOREIGN PATENT DOCUMENTS

| | | |
|---|---|---|
| WO | WO 91/03982 | 4/1991 |
| WO | WO 03/065907 | 8/2003 |
| WO | WO 2006/107222 | 10/2006 |
| WO | WO 2008/017501 | 2/2008 |
| WO | WO 2012/162607 | 11/2012 |
| WO | WO 2012/162608 | 11/2012 |

* cited by examiner

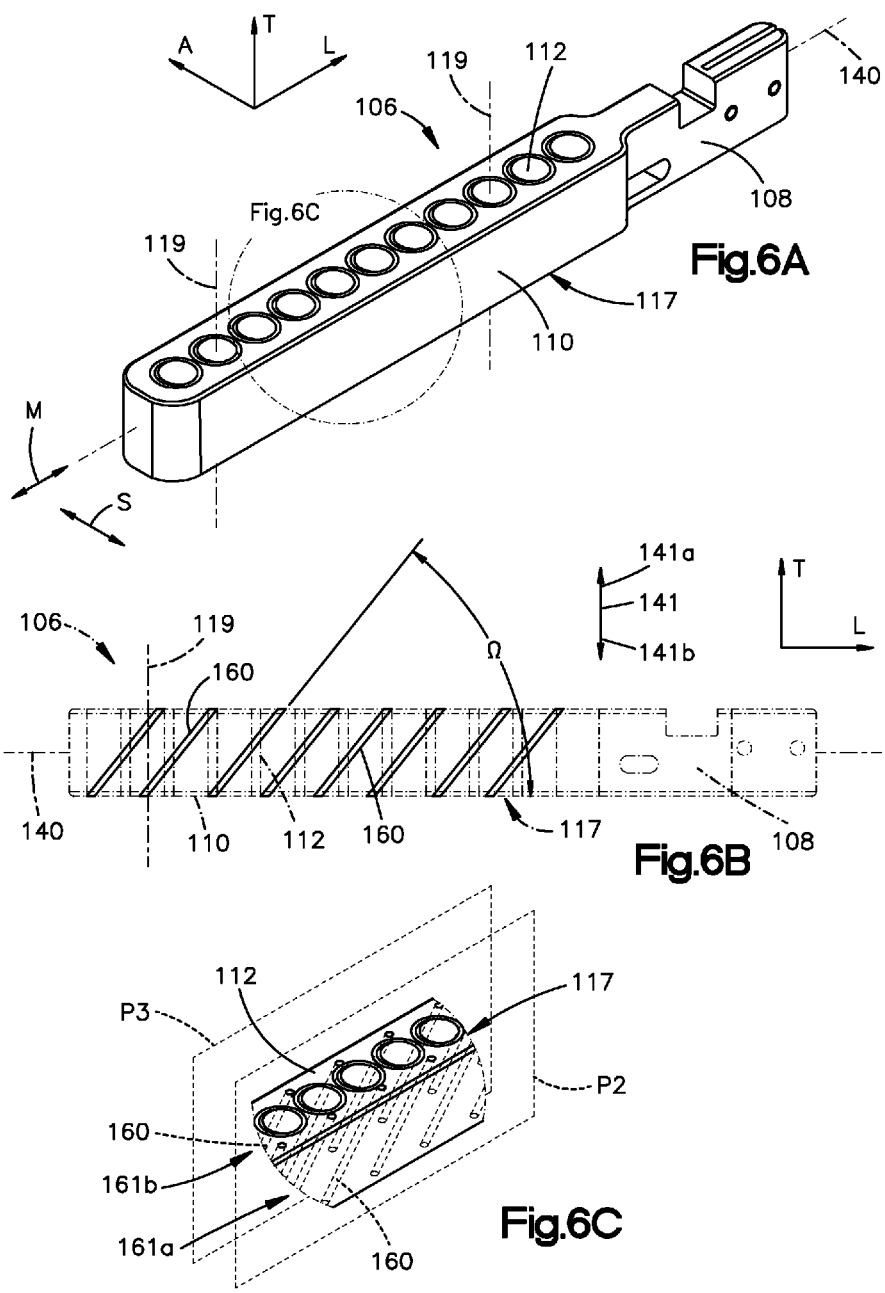

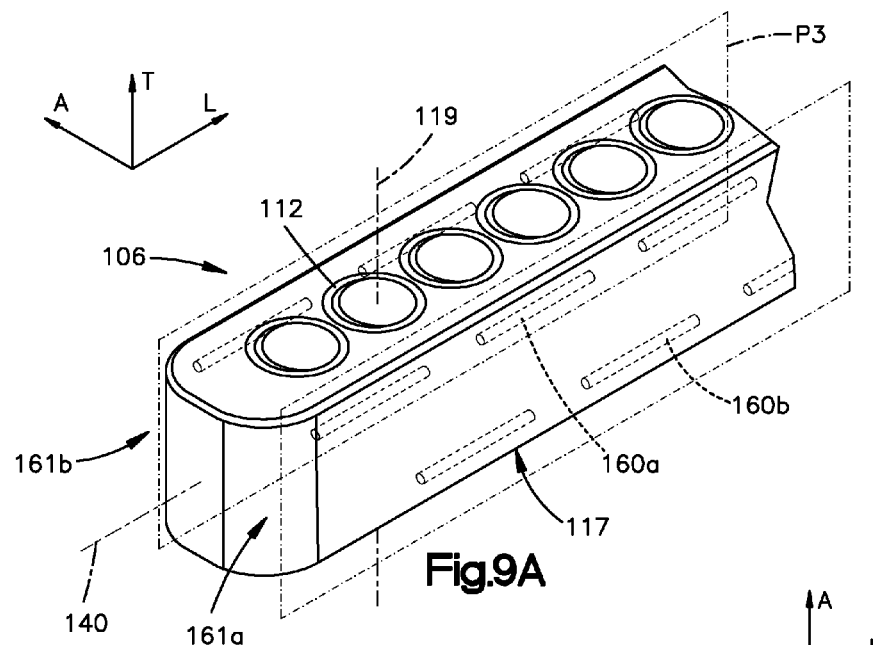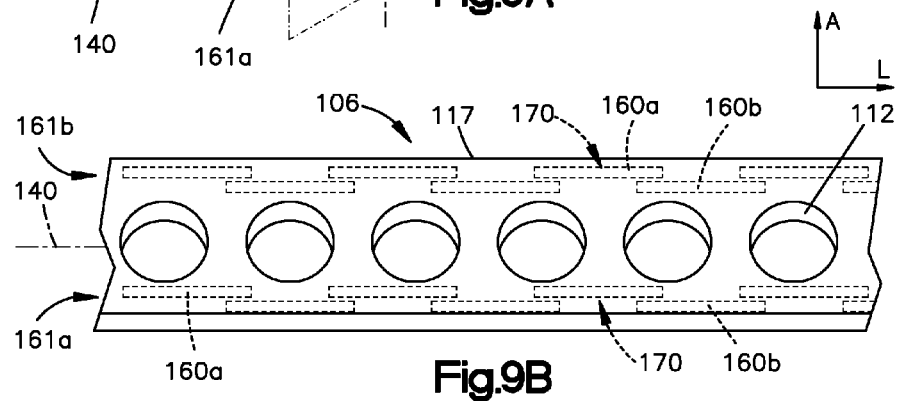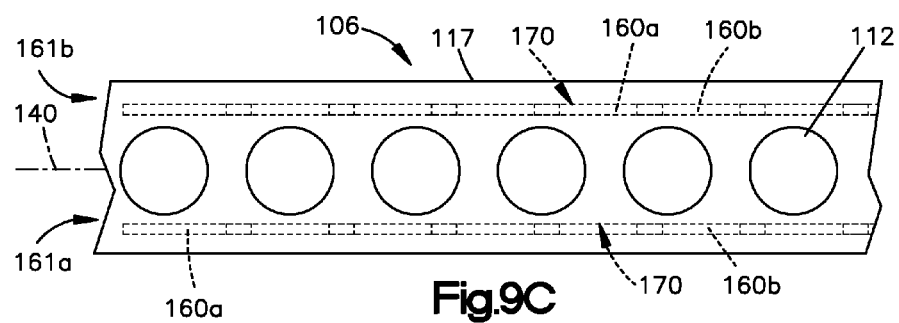

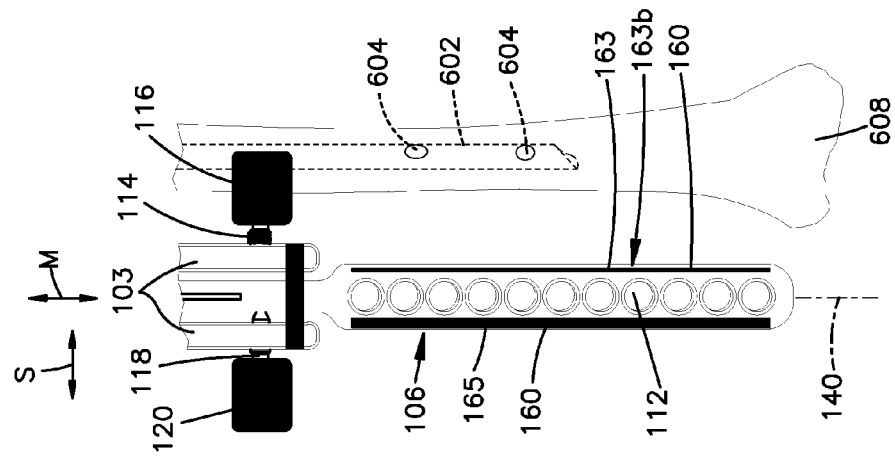
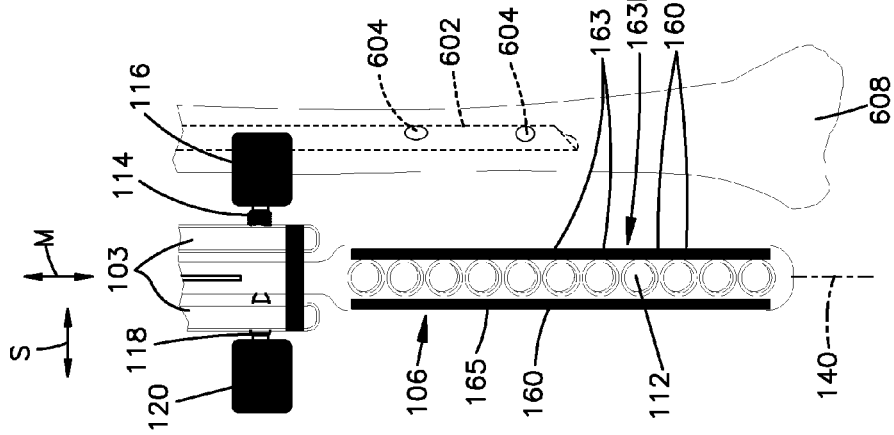
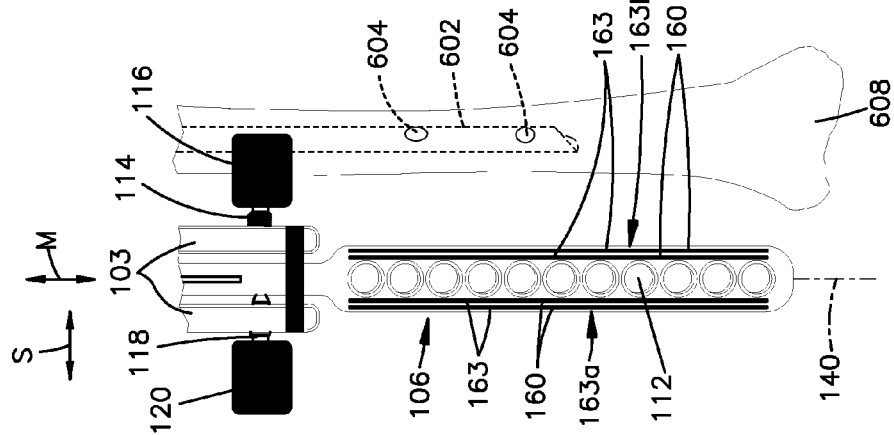

US 8,986,315 B2

AIMING DEVICE HAVING RADIO-OPAQUE MARKERS

CROSS-REFERENCE TO RELATED APPLICATIONS

This claims the benefit of U.S. Provisional Patent Application Ser. No. 61/489,930 filed on May 25, 2011 and U.S. Provisional Patent Application Ser. No. 61/501,868, filed Jun. 28, 2011, the disclosure of each of which is hereby incorporated by reference as if set forth in its entirety herein.

TECHNICAL FIELD

The present disclosure relates to the fields of bone implants and bone fixation devices.

BACKGROUND

To stabilize fractured bones (including so-called long bones such as femurs, tibias, fibulas, humeri, radii, ulnas, metacarpals, metatarsals, and phalanges), users have employed intramedullary rods or nails to provide structural reinforcement to the bone. Such devices may be anchored, for instance in the medullary canal of the bone, by way of screws inserted through the bone (in a direction transverse to the major axis of the nail) so as to engage with locking holes in the nail.

Some bones, however, have a natural curvature, and intramedullary devices inserted into the medullary canal can deflect so as to conform to this curvature. Accordingly compensation for the curvature of the bone allows for accurate placement of the fixation screws when the screws are aimed and then inserted through the skin and bone to engage with the locking holes of the intramedullary device.

SUMMARY

In one embodiment, an aiming arm is configured to be aligned with an implant. The aiming arm includes a body that defines a plurality of apertures configured to receive respective fixation members. The aiming arm further includes at least a pair of radio-opaque markers carried by the body, wherein when a radiographic image is taken of the aiming arm from a first viewpoint, the radio-opaque markers define a first radiographic image characteristic when the aiming arm is not aligned with a source of the radiographic image, and the radio-opaque markers define a second radiographic image characteristic when the aiming arm is aligned with the source.

BRIEF DESCRIPTION OF THE DRAWINGS

The summary, as well as the following detailed description, is further understood when read in conjunction with the appended drawings. For the purpose of illustrating the present disclosure, there are shown in the drawings exemplary embodiments of the disclosure; however, the disclosure is not limited to the specific methods, compositions, and devices disclosed. In addition, the drawings are not necessarily drawn to scale. In the drawings:

FIG. 6A is a perspective view of the aiming arm illustrated in FIG. 1A;

FIG. 6B is a side elevation view of the aiming arm illustrated in FIG. 6A, showing a plurality of radio-opaque alignment markers;

FIG. 6C is a perspective view of a portion of the aiming arm illustrated in FIG. 6A, taken along line 6C;

FIG. 9A is a perspective view of the aiming arm including a plurality of radio-opaque markers in accordance with another embodiment;

FIG. 9B is a schematic view of a radiographic image of a portion of the aiming arm as illustrated in FIG. 9B, showing the radio-opaque markers in a misaligned configuration; and FIG. 9C is a schematic view of the radiographic image illustrated in FIG. 9B, showing the radio-opaque markers in an aligned configuration.

FIGS. 10A-10C are top plan views of implantation assemblies, but showing the aiming arm as including a radio-opaque material in accordance with various embodiments;

DETAILED DESCRIPTION

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Figure 1A:
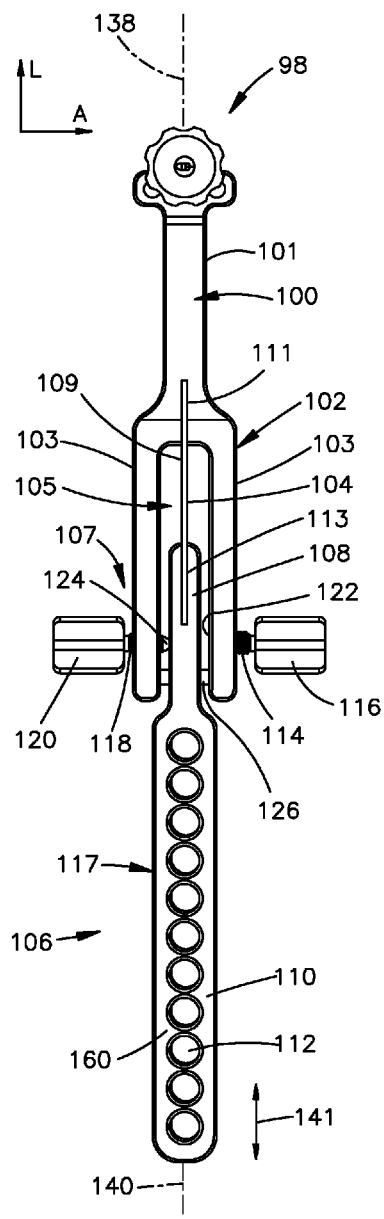
FIG. 1A is a top plan view of an aiming device constructed in accordance with one embodiment including a base and an aiming arm configured to be coupled to the base.
Figure 1B:
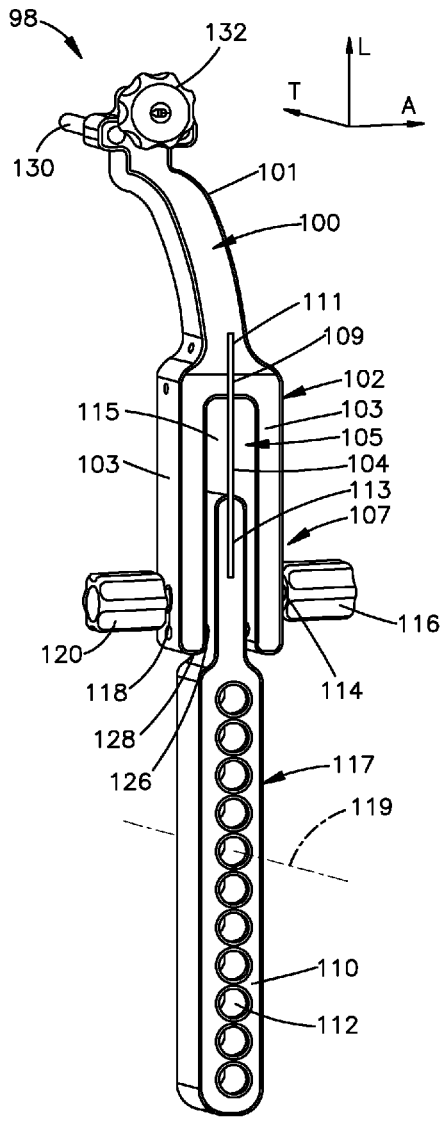
FIG. 1B is a perspective view of the aiming device illustrated in FIG. 1B.
Figure 2:
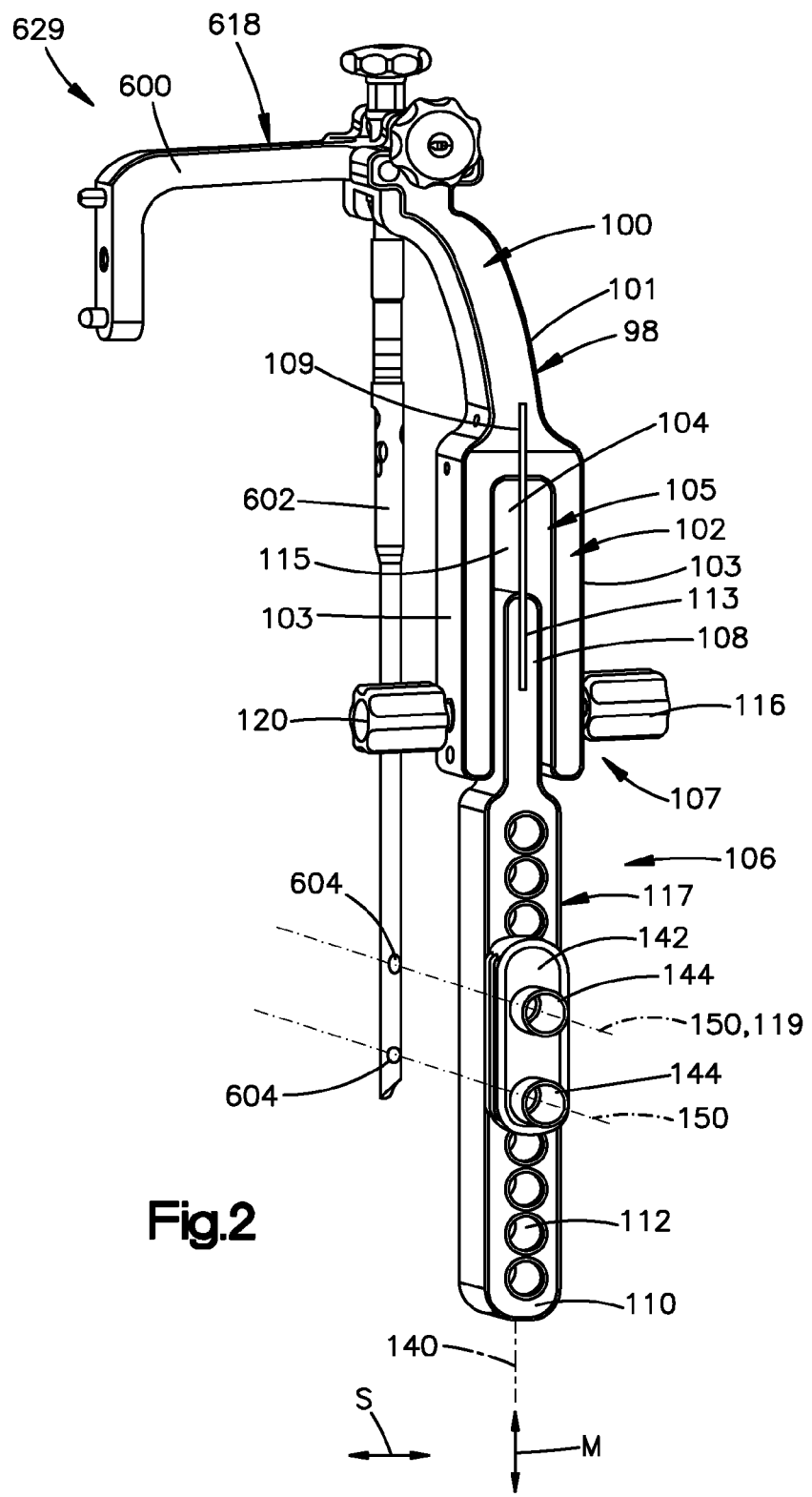
FIG. 2 is a perspective view of a bone fixation system including a support frame, an intramedullary nail, the aiming device illustrated in FIG. 1A supported by the support frame, and a mask coupled to the aiming arm.
Figure 3:
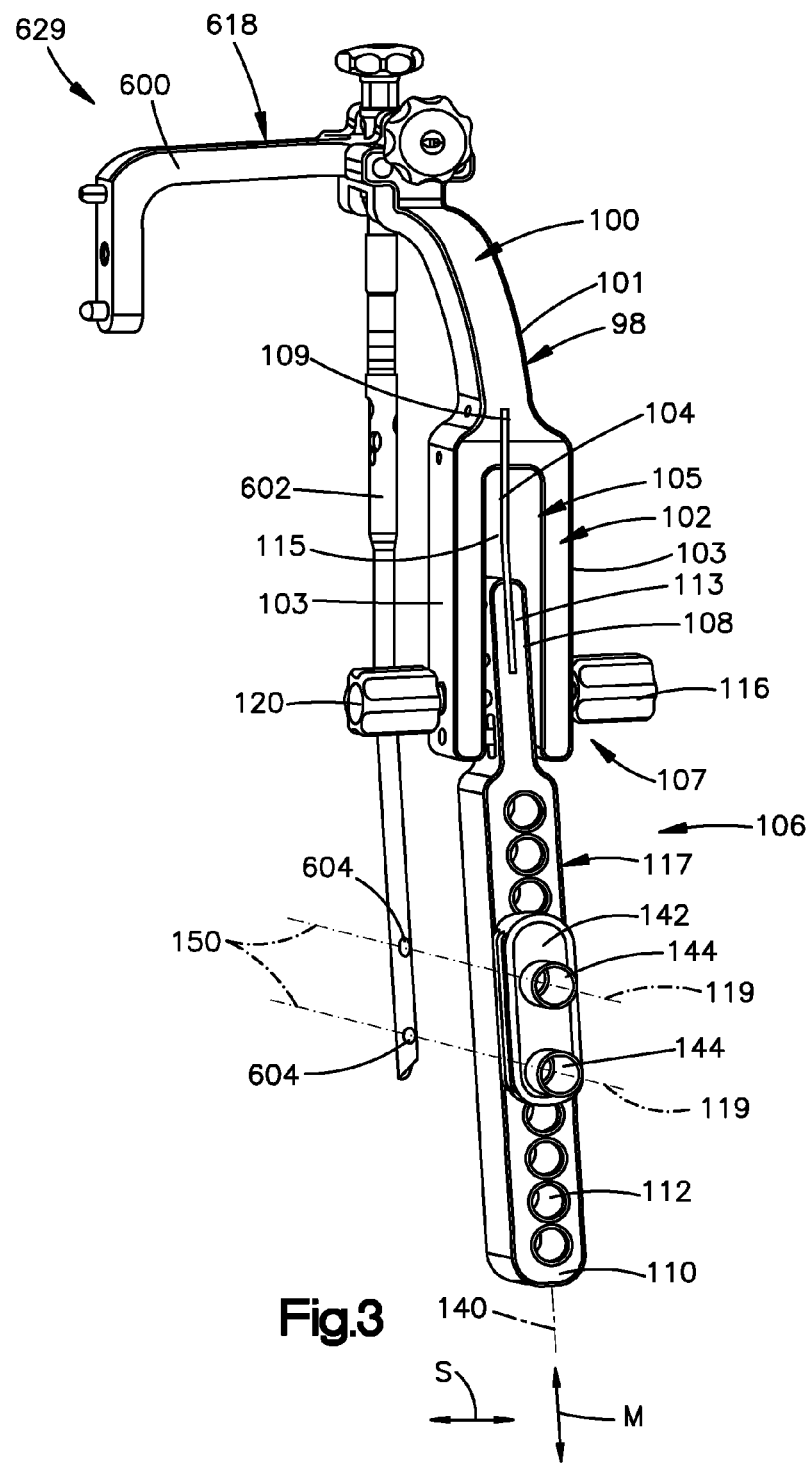
FIG. 3 is a perspective view of the bone fixation assembly illustrated in FIG. 2, showing the intramedullary nail in an inserted, deflected configuration and showing the aiming arm in a corresponding deflected configuration.
Figure 4:
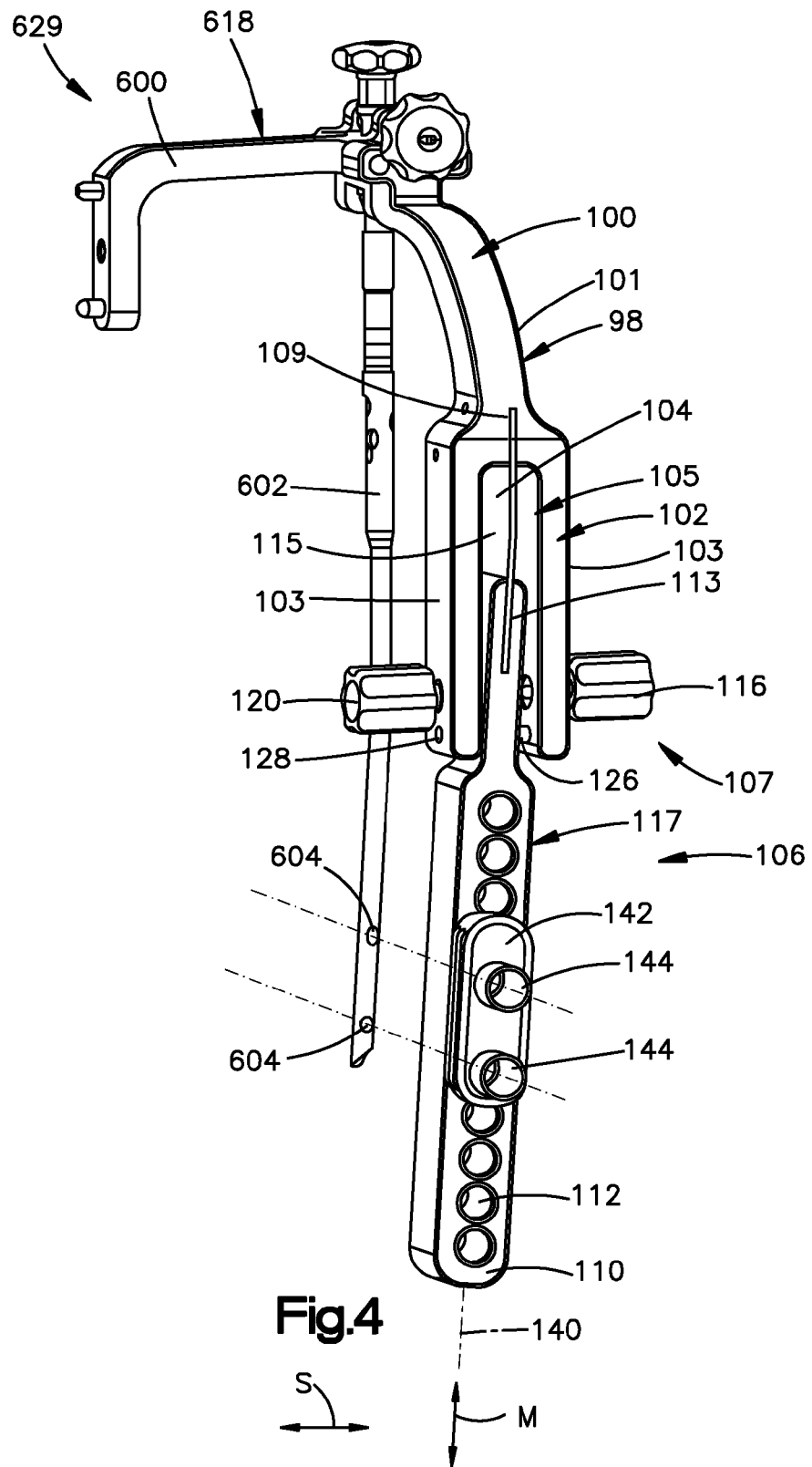
FIG. 4 is a perspective view of the bone fixation assembly illustrated in FIG. 3, showing the intramedullary nail in another deflected configuration and showing the aiming arm in a corresponding deflected configuration.

Referring initially to FIGS. 1A-2, an aiming device 98 includes a base 100 and an elongate aiming arm 106 that is supported by the base 100. In accordance with one embodiment, the aiming arm 106 can be movable with respect to the base 100. The base 100 and the aiming arm 106 can be arranged such that the base 100 is disposed proximal with respect to the aiming arm 106. The base 100 of the aiming device 98 is elongate along a central axis 138 that extends along a longitudinal direction L. The base 100 may include a spacer 101, for instance at its proximal end, and a forked projection 102 that extends distally from the spacer 101 and can thus define the distal end of the base 100. The forked projection 102 includes a pair of legs 103 that are spaced along a lateral direction A that is substantially perpendicular to the longitudinal direction L. Thus, the aiming device 98 can include a length along the longitudinal direction L, a width along the lateral direction A, and a thickness along a transverse direction T that is substantially perpendicular to both the longitudinal direction L and the lateral direction A.

The legs 103 can be spaced and arranged such that the projection 102 defines a C-shape, a U-shape, a Y-shape, or any suitable alternative shape as desired, such that the projection 102 defines a gap 105 that is defined between the legs 103. The aiming arm 106 can include an arm body 117 that is elongate substantially along a respective major axis 140 that extends along a major direction M (see FIG. 2). The major direction M can be coincident with the longitudinal direction L or any alternative direction as desired. The aiming arm 106 can define a proximal portion 108 and an opposed distal portion 110 that is spaced from the proximal portion 108 along the major direction M. In accordance with the illustrated embodiment, the proximal portion 108 is disposed closer to the base 100 than the distal portion 110. The distal portion 110 can define a lateral width that can be different than, for instance greater than as shown in FIG. 1A or less than, that of the proximal portion 108. Alternatively, the lateral width of the distal portion 110 can be the same as that of the proximal portion 108.

The lateral width of a portion of the aiming arm 106, such as the proximal portion 108, can be less than the lateral width of the gap 105, such that the proximal portion 108 can be positioned in the gap 105 between the legs 103. Alternatively or additionally, the distal portion 110 of the aiming arm 106 may be positioned between the legs 103.

The aiming device 98 can further include an adjustment assembly 107 that is configured to adjust at least one of a directional (e.g., lateral) position and an angular orientation, collectively referred to herein as a position, of the aiming arm 106 relative to the base 100. For instance, the adjustment assembly 107 can include a biasing member 109 that is connected to and between the base 100 and the aiming arm 106. In accordance with one embodiment, the biasing member 109 can be configured as a spring 104. The spring 104 can be configured as a leaf spring, as shown in FIG. 1A, a coil spring, or any suitable alternative spring or alternatively constructed biasing member as desired. The biasing member 109 is configured to allow motion of the aiming arm 106 in a particular direction, such as the lateral direction A. The biasing member 109 is disposed between the projections 102, so as to flexibly connect the aiming arm 106 to the base 100. In accordance with the illustrated embodiment, the base 100 defines a slot 111 that extends transversely into or through the spacer 101. The slot 111 is configured to receive the biasing member 109 such that the biasing member 109 is secured in the slot 111. The biasing member 109 can define a plate 115 that can be supported by the base 100 in an orientation that is substantially planar in the longitudinal and transverse directions. Thus, the biasing member 109 is supported by the base 100 so as to be laterally flexible toward and away from each of the legs 103 and less flexible or substantially rigid with respect to the transverse direction T. Likewise, the aiming arm 106 can define a slot 113 that extends transversely into or through the proximal portion 108. The slots 111 and 113 are configured to receive opposed ends of the biasing member 109. It should be appreciated that the biasing member 109 can be flexibly connected between the base 100 and the aiming arm 106 in any suitable alternative manner as desired.

Figure 5:
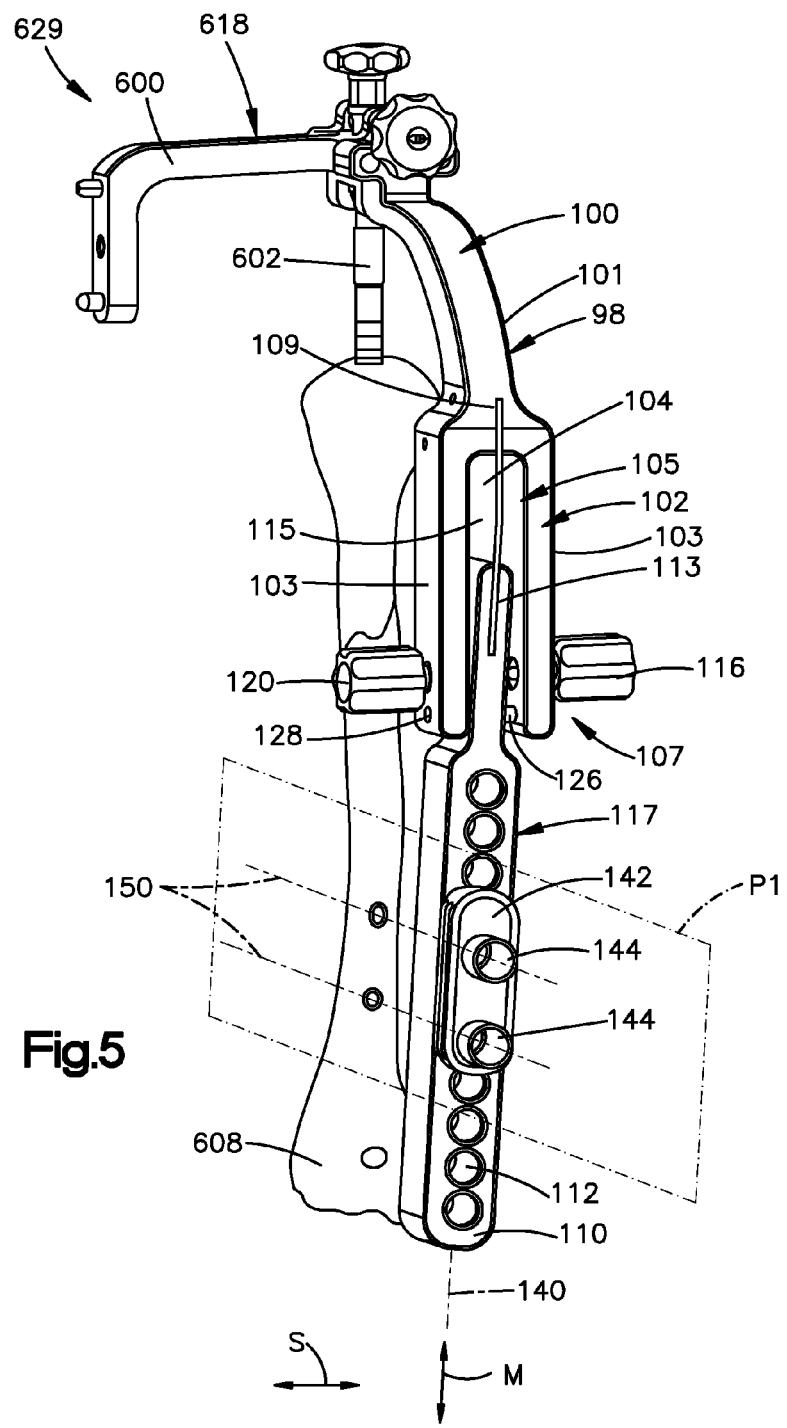
FIG. 5 is a perspective view of the implantation assembly as illustrated in FIG. 10, showing the intramedullary nail implanted in a long bone.

The aiming arm 106 can define an arm body 117 that defines at least one aperture, such as a plurality of apertures 112 that can define at least a first aperture 112 and a second aperture 112. The apertures 112 can extend through the distal portion 110 along the transverse direction T. The apertures 112 can be spaced along the major axis 140, and can be defined by respective transverse central axes 119 that extend substantially along the transverse direction L and are aligned along the longitudinal direction L, and can coincide with the major axis 140, which can bisect at least a pair of, up to all of, the apertures 112. It should thus be appreciated that the major axis 140 can be a central axis of the arm body 117, or can be offset from the central axis of the arm body 117, and can extend along the longitudinal direction L or along a direction offset from the longitudinal direction L as desired. As illustrated in FIG. 5, the central axes 119 of the apertures 112 are aligned along a first plane P1 that can be defined by the major axis 140 of the aiming arm 106 and the central axes of the apertures 112. Thus, the central axes 119 extend along the first plane P1 and are spaced along the first plane P1. The apertures 112 can be suitably configured to receive respective fixation members, such as guiding sleeves, screwdrivers or other aids to place complementary screws, bolts, pins, pegs, or other locking members. The locking members in turn engage with apertures (which may be termed locking holes) disposed in an intramedullary nail that has been installed in a bone, as discussed and described elsewhere herein in further detail.

The apertures 112 of the aiming arm 106 may be of a diameter suitable for user with the appropriate locking screw. Such diameters can be in the range of from 1 mm to 20 mm, or from 2 mm to 18 mm, or from 5 mm to 15 mm, or even about 10 mm. The apertures may be spaced apart by regular increments, e.g., by 10 mm, 15 mm, 20 mm, or 25 mm. The spacing of the apertures 112 of the aiming arm 106 may depend, for instance, on the spacing between the apertures on the intramedullary nail being fixed, such that at least one such as a plurality of the apertures 112 can be selectively aligned with a corresponding at least one such as a plurality of apertures 164 of the intramedullary nail 162.

The adjustment assembly 107 further includes at least one knob such as a pair of knobs 116 and 120 and corresponding opposed movable members 114 and 118 that are attached to the knobs 116 and 120 and can define pusher members configured to engage the aiming arm 106. For instance, the movable members 114 and 118 may be screws, bolts, and the like. The opposed movable members 114 and 118 can be supported by one of the legs 103 and laterally aligned with each other, such that a lateral axis extends through both movable members 114 and 118. It should be appreciated in accordance with an alternative embodiment that the movable members 114 and 118 can be laterally offset. The movable members 114 and 118 are configured to translate laterally so as to bear against the aiming arm 106, such as the proximal portion 108, and bias the aiming arm 106 toward the opposed leg 103. Thus, the movable members 114 can define pusher members configured to bias the aiming arm 106, such as the proximal portion 108 of the aiming arm 106, away from the respective leg 103 and at least one of laterally offset and angularly offset with respect to the base 100, such that the major axis 140 of the aiming arm 106 and the longitudinal axis 138 of the base 100 are not aligned. Alternatively, the movable members 114 can be attached to the proximal portion so as to provide pull members that can pull the proximal portion 108 as they move laterally.

In accordance with the illustrated embodiment, the movable members 114 and 118 are threadedly supported by the legs 103 and rotatably coupled to the respective knobs 116 and 120, such that rotation of the knobs 116 and 120 causes the movable members 114 and 118 to correspondingly rotate. Accordingly, rotation of the respective knobs 116 and 120 in a first direction causes the movable members 114 and 118 to extend deeper into the gap 105, while rotation of the respective knobs 116 and 120 in an opposite second direction causes the movable members 114 and 118 to retract from the gap 105. Thus, each of the knobs can be selectively rotated (e.g., by turning) to adjust the position of the opposed movable members 114 and 118, which in turn adjusts the position of the aiming arm 106 and the deflection of the biasing member 109. For instance, the biasing member 109 can apply a force against the aiming arm 106 as it travels in response to the biasing force applied against the aiming arm 106 by the movable members 114 and 118, thereby retaining the arm, and in particular the proximal portion 108, against the movable members 114 and 118. The opposed movable members 114 and 118 may include an end 124, which can contact and apply a biasing force to the aiming arm 106. The opposed members 114 and 118 may alternatively or additionally be positioned to adjustably contact and apply a biasing force to the biasing member 109, such as the plate 115. Accordingly, the opposed movable members 114 and 118 may deflect the biasing member 109 directly, which in turn adjusts the position of the aiming arm 106. In both embodiments, it should be appreciated that the members 114 and 118 apply a biasing force to the aiming arm 106, for instance directly to the aiming arm 106 or indirectly via the biasing member 109.

The opposed movable members 114 and 118 can be suitably adjusted so as to secure the aiming arm 106 in a desired position, for instance by moving at least one or both of the members 114 and 118 so as to achieve a desired deflection of the biasing member 109 or the aiming arm 106.

The aiming arm 106 may be positioned in a number of ways. In one embodiment, the user may retract both opposed members 114 and 118 and then extend one of the opposed members 114 and 118 into the gap 105 so as to operatively engage the aiming arm 106 so as to apply a biasing force to the aiming arm 106 until the aiming arm 106 reaches the desired position. The user may then bring the other of the opposed member 114 and 118 against the aiming arm 106 so as to releasably lock the aiming arm 106 in the desired position. The opposed members 114 and 118 may have end caps 122 and 124, respectively, that are configured to contact the aiming arm 106. As shown in the illustrative figure, the opposed members 114 and 118 may be screws, and can thus be referred to herein as set screws. One or both of the caps 122 and 124 may be hardened. Alternatively, one or both of the caps 122 and 124 may be deformable.

The adjustment assembly 107 may also include a guide member 126 that guides movement of the aiming arm 106. For instance, the guide member 126 can be secured to either or both of the opposed legs 103 and configured to restrict rotation of the aiming arm 106. The guide member 126 can be configured as a rod, a peg, or any suitable alternative shape as desired. The guide member 126 extends through a longitudinally elongate aperture 128 defined by in the aiming arm 106. The guide member 126 can engage the hole 128 so as to allow the aiming arm 106 to deflect laterally (e.g., right or left in the illustrated orientation such that the axes 138 and 140 are angularly offset with respect to each other) and restrains the aiming arm 106 from deflecting into or outward from the plane of the figure. The guide member 126 permits deflection of the elongate arm and spring 104 in the lateral direction A, but limits or prevents deflection in the transverse and longitudinal directions T and L.

The aiming device 98 can be configured such that the aiming arm 106 and spring 104 are deflected to the left. To achieve this deflection, the opposed right-hand member 114 may be tightened (not shown) so as to deflect the elongate arm and spring 104 to the left. This deflection may also entail retracting the left-hand opposed member 118 so as to permit the desired amount of deflection of the spring 104. Once the spring 104 and aiming arm 106 are deflected, the left-hand opposed member 118 may be tightened so as to lock the arm (and spring) into place.

The aiming device 98 can further be configured such that the aiming arm 106 and spring 104 are deflected to the right. To achieve this deflection, the opposed left-hand member 114 may be tightened (not shown) so as to deflect the elongate arm and spring 104 to the right. This deflection may also entail retracting the right-hand opposed member 118 so as to permit the desired amount of deflection of the spring 104. Once the spring 104 and aiming arm 106 are deflected, the right-hand opposed member 118 may be tightened so as to lock the arm (and spring) into place.

Referring now to FIGS. 2-5, a bone fixation system 629 can include the aiming device 98 and an implantation assembly 618 that, in turn, can include a support frame 600 and an intramedullary nail 602 that can be supported by the support frame 600, implanted into a long bone 608 such as a humerus, a femur, or the like, and subsequently detached from the support frame 600. The intramedullary nail 602 may include apertures 604 that receive screws, rods, pegs, or other fixation members to anchor the nail in the bone. The intramedullary nail 602 may be attached to the support frame 600 in such a manner that the intramedullary nail 602 is elongate along a direction that is substantially parallel to the major axis 140 of the aiming arm 106. The apertures 112 of the aiming arm 106 may be placed into alignment with one or more apertures 604 of the intramedullary nail 602 when the intramedullary nail 602 has been attached to the support frame 600 and implanted into the bone 608, such that bone anchors (e.g., a screw) driven through select ones of the apertures 112 of the aiming arm 106 can further be driven into or through corresponding select ones of the apertures 604 of the intramedullary nail 602. Accordingly, screws, nails, pegs, and the like may be inserted through the apertures 112 of the aiming arm 106 and mate with the intramedullary nail 602, for instance at the apertures 604. The apertures 604 of the nail may be at least partially or fully unthreaded, or at least partially or fully threaded so as to engage a complementary thread on a fixation member (e.g., a screw, peg) that is inserted through an aperture 112 of the aiming arm 106. The aperture 604 may also be splined so as to engage a complementary structure on a fixation member (e.g., a screw, peg) inserted through an aperture 112 of the aiming arm 106.

The aiming device 98 can also include a mask 142 that is configured to be coupled to the aiming arm 106, for instance at one or more of the apertures 112 of the aiming arm 106 so as to identify one or more select ones of the apertures 112 that are intended to receive a fastener so as to couple the aiming arm 106 to the intramedullary nail 602. The mask 142 may be made of a material that differs (e.g., in color, in material) from the material of the aiming arm 106. This in turn assists the user in identifying which particular apertures 112 in the aiming arm 106 have been identified to receive nails, screws, or other fixation members that anchor a nail into a patient. For example, the mask 142 may be made from a blue or red material, which in turn directs the user's attention to apertures 144 of the mask 142 that are intended to be used for a given procedure.

The mask 142 may also include a radio-opaque material, which material allows the user to locate the mask on a radiographic image. The radio-opaque material of the mask 142 may be disposed about the edge or periphery of the mask 142 or at another predetermined location of the mask 142 to allow the user to locate the mask 142 on a radiographic image. The radio-opaque material may also be disposed around or near the apertures of the mask so as to facilitate the user's alignment of the apertures 144 relative to the apertures or fixation holes of the intramedullary rod or nail.

The mask 142 may also include one or more projections that allow the user to seat the mask onto the elongate arm. Such projections may engage the aiming arm 106 and can further enter into apertures 112. The mask 142 may include one or more apertures 144 that are aligned with select ones of the apertures 112 of the elongate arm so as to identify those select apertures 112 that are aligned with complementary apertures 604 of the intramedullary nail 602. Thus, a radiographic image can identify the mask 142 and the apertures 112 that are operatively aligned with the complementary apertures 601 and 604 of the intramedullary nail 602. The aiming arm 106 defines at least one transverse guide path 150 such as a plurality of transverse guide paths 150 that are coincident with the respective central axes of the one or more select apertures 112. The guide paths 150 illustrate that the mask apertures 144 are in alignment with apertures 112 of the aiming arm 106, which paths are followed by fixation members that are inserted through the aiming arm 106 of the aiming assembly into the intramedullary nail 602 when the aiming arm 106 and the intramedullary nail 602 are aligned. Thus, the aiming arm 106 can define at least one aperture 112, and the mask 142 can define at least one aperture 144 that define respective central axes that are coincident with the guide path 150. The aiming arm 106 can be position such that the guide path 150 can be coincident with a respective at least one central axis 604 of the intramedullary nail 602.

Referring now to FIG. 5 in particular, the intramedullary nail 602 is shown inserted into the long bone 608 in a deflected state, for instance angularly offset from the longitudinal direction L. Thus, the aiming arm 106 of the aiming device 98 can be correspondingly deflected such that the apertures 144 of the mask 142 and the apertures 112 of the aiming arm 106 are aligned with the apertures 604 of the intramedullary nail 602, as illustrated by the alignment paths 150 illustrate a trajectory of a fixation member (e.g., a screw, peg) that is inserted through apertures 112 of the elongate arm and apertures 144 of the mask 142 and into or through the apertures 604 of the intramedullary nail 602 to anchor the intramedullary nail 602 to the aiming arm 106.

Referring now to FIGS. 6A-C, the aiming arm 106 can include at least one radio-opaque marker 160 such as a plurality of radio-opaque markers 160 that are configured to indicate whether a radiographic image source is at least partially aligned with the aiming arm 106. For instance, the opaque markers 160 are configured to provide an indication whether the radiographic image source is aligned with the aiming arm 106 along the major direction M, or whether movement of the radiographic image source along a direction substantially perpendicular to the major direction M with respect to the aiming arm 106 will bring the radiographic image source in alignment with the aiming arm 106 along the major direction M. Once the radiographic image source is aligned with the aiming arm 106, a determination can be made as to whether the select apertures 112 of the aiming arm 106 are operably aligned with the corresponding apertures 604 of the intramedullary nail 602 when the intramedullary nail 602 has been implanted in the long bone 608. The radio-opaque markers 160 can be made from any suitable radio-opaque material, and can be in the form of pellets that are injected into the aiming arm 106, or any alternative structure suitable to be carried by the aiming arm 106 so as to define an alignment guide that indicates whether the radiographic source is aligned with the aiming arm 106.

For instance, the radiographic source can be said to be at least partially aligned with the aiming arm 106 when the radiographic beams of the radiographic image source extend along a direction that that intersects the central axes 119 of the select apertures 112 of the aiming arm 106, such that the radiographic source can define a view to the aiming arm 106 that is directed substantially parallel to the central axis 119 of each of the select apertures 112, and further substantially parallel to the major axis 140 of the aiming arm 106. When the radiographic image source is aligned with the aiming arm 106, it can be concluded whether the select apertures 112 are aligned with the underlying apertures 604 of the intramedullary nail 602 upon visual inspection of a radiographic image produced by the radiographic source. The resulting radiographic image can include at least a portion of the aiming arm 106 (including at least one of the apertures 112) and at least a portion of the intramedullary nail 602 (including at least one of the apertures 604). For instance when the radiographic image that illustrates that the apertures 112 and 604 substantially coincide with each other when the radiographic source is aligned with the aiming arm 106, it can be concluded that the central axes 119 of the select apertures 112 substantially coincide with the central axes the underlying apertures 604. Accordingly, a sleeve, fastener, or other fixation device driven through the select apertures 112 along the respective central axes of the select apertures 112, for instance along the guide path 150, will further extend through the underlying apertures 604 of the intramedullary nail 602.

If, on the other hand, the radiographic source is not aligned with the aiming arm 106 with respect to the axis, such that the radiographic source defines a view to the aiming arm 106 that is angularly offset with respect to the central axis 119 of each of the select apertures 112, the resulting radiographic image might illustrate that the apertures 112 and 604 substantially coincide and are therefore aligned when in fact a sleeve, fastener, or other fixation device that extends through the apertures 112 along the respective central axes of the apertures 112 toward the intramedullary nail 602 will not, in fact, extend through the apertures 604 of the intramedullary nail 602. Thus, it can be said that the radio-opaque markers 160 can be visible in a radiographic image (for instance, during real-time radiography) so as to assist in visual alignment of the aiming arm 106, including at least one of the apertures 112, with at least one complementary aperture 604 on the intramedullary nail 602 or other fixation member.

In accordance with one embodiment illustrated in FIGS. 6B-C, the radio-opaque markers 160 are illustrated as elongate along a direction oblique with respect to the transverse direction T, and thus also oblique with respect to the guide paths 150 (see FIGS. 2-5) so as to define a non-zero angle Ω with respect to an axis that extends substantially parallel to the major axis 140. The radio-opaque markers 160 can further be arranged in at least one row 161a such as a pair of rows 161a and 161b of radio-opaque markers 160 that are spaced along the longitudinal direction L. The rows 161a and 161b are positioned on opposite sides of the apertures 112 along a direction that extends substantially perpendicular to the major axis 140, the direction defining a select direction S. The apertures 112 can be equidistantly spaced from the rows 161a and 161b along the select direction S as desired. The radio-opaque markers 160 of each of the rows 161a and 161b can be aligned with the other radio-opaque markers 160 of the respective row along a direction that is substantially parallel to the major axis 140. Otherwise stated, each of the radio-opaque markers 160 of each of the first and second rows 161a and 161b can define the same distance to the major axis 140 (see FIG. 1A) of the aiming arm 106 along the select direction S.

Thus, each of the radio-opaque markers 160 can be oriented such that the markers 160 are elongate along a direction that includes directional components that includes the major direction M and further includes the transverse direction T, but does not include a directional component along the select direction S, which can be oriented substantially perpendicular to the major axis 140 of the aiming arm 106 in accordance with the illustrated embodiment. As a result, when the radiographic image source produces an image that illustrates all of the radio-opaque markers 160 are in alignment, it can be concluded that the radiographic image source is aligned with the central axis of the apertures 122, at least along the select direction S.

Furthermore, in accordance with the embodiment illustrated in FIGS. 6B-C, the radio-opaque markers 160 of each respective row 161a and 161b are discontinuous and therefore spaced from each other, for instance along the major direction M of the aiming arm 106, which is substantially perpendicular to the select direction S, though it should be appreciated that the aiming arm 106 can include radio-opaque markers 160 of each respective row 161a and 161b that are continuous with each other along the major direction M, as described in more detail below.

With continuing reference to FIG. 6C, each radio-opaque marker 160 of the first row 161a is aligned along a second plane P2, and each radio-opaque marker of the second row 161b is aligned along a third plane P3. Thus, each radio-opaque marker 160 of the first row 161a extends, or is elongate, along the second plane P2, and each radio-opaque marker 160 of the first row 161a is spaced along the second plane P2. Likewise, each radio-opaque marker 160 of the second row 161b extends, or is elongate, along the third plane P3, and each radio-opaque marker 160 of the second row 161b is spaced along the third plane P3. The second and third planes P2 and P3 are substantially parallel to the first plane P1 (FIG. 5), and can further be coincident with the first plane P1 if desired. It should be appreciated that the radio-opaque markers 160 can be aligned in a single plane that is parallel with the first plane P1. Furthermore, the plane can be coincident with the first plane P1 if desired.

As illustrated in FIGS. 6B-C, at least a pair of the radio-opaque markers 160 of the first row 161a, and thus on the second plane P2, (such as adjacent radio-opaque markers 160 of the second plane P2) define a location, which can be a point, such that the respective locations of the pair of radio-opaque markers 160 are offset from each other along an axis 141. The axis 141 is illustrated as an axis that extends along the transverse direction T, and thus substantially perpendicular to the major direction M and the select direction S. The axis 114 is further substantially parallel to the central axes 119 of the apertures 112 (and can further be coincident with the central axis 119, depending on the location of the second plane P2), or substantially perpendicular to the major axis 140 of the aiming arm 106. For instance, the leading edge of a first radio-opaque marker 160 is offset from the trailing edge of a second adjacent radio-opaque marker 160 along a first direction 141a on the axis 141, while the trailing edge of the first radio-opaque marker 160 is offset from the leading edge of the second adjacent radio-opaque marker 160 along a second direction 141b on the axis 141 that is opposite the first direction 141a.

Similarly, at least a pair of the radio-opaque markers 160 of the second row 161b, and thus on the third plane P3 (such as adjacent radio-opaque markers 160 of the third plane P3), define a location, which can be a point, such that the locations are offset from each other along the axis 141, which can be substantially parallel to the central axes 119 or substantially perpendicular to the major axis 140. For instance, the leading edge of a first radio-opaque marker 160 is offset from the trailing edge of a second adjacent radio-opaque marker 160 along a first direction 141a on the axis 141, while the trailing edge of the first radio-opaque marker 160 is offset from the leading edge of the second adjacent radio-opaque marker 160 along a second direction 141b on the axis 141 that is opposite the first direction 141a. The first direction 141a can be directed outward away from the underlying bone that receives the intramedullary nail 162 and the second direction can be direction inward toward the underlying bone.

Thus, a portion of one of the radio-opaque markers of the first row 161a or the second plane P2 is offset with respect to a portion of another one (such as an adjacent one) of the radio-opaque markers of the first row 161a or the second plane P2 along the axis 141, and a portion of one of the radio-opaque markers of the second row 161b or the third plane P3 is offset with respect to a portion of another one (such as an adjacent one) of the radio-opaque markers 160 of the second row 161b or the third plane P3 along the axis 141

Accordingly, referring now to FIGS. 7A-8C, when a radiographic image source is offset from an aligned position with respect to the aiming arm 106 along the select direction S from (such that the radiographic image source is not oriented substantially parallel to the central axes 119), the radio-opaque markers present a nonlinear (for instance jagged) line 170 along the major direction M. The line 170 becomes increasingly jagged as the radiographic image source is increasingly angularly offset from the central axes of the select apertures 112 along the select direction S, and becomes less jagged as the radiographic image source is brought into alignment with the central axis 119 of the select apertures 112, such that the angle defined by the radiographic image source and the central axis 119 decreases. Furthermore, the radiographic image source can be offset with respect to the apertures 112 along the major direction M of the aiming arm 106 (see FIG. 2).

Figure 7A:
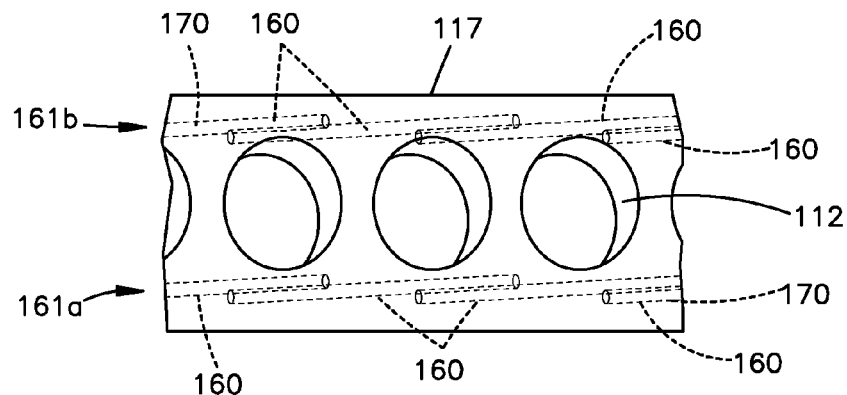
FIG. 7A is a perspective view of a radiographic image of a portion of the aiming arm illustrated in FIG. 6C as taken from a radiographic image source, showing the radio-opaque alignment markers in a misaligned configuration, and further showing apertures of the aiming arm in a misaligned configuration.
Figure 7B:
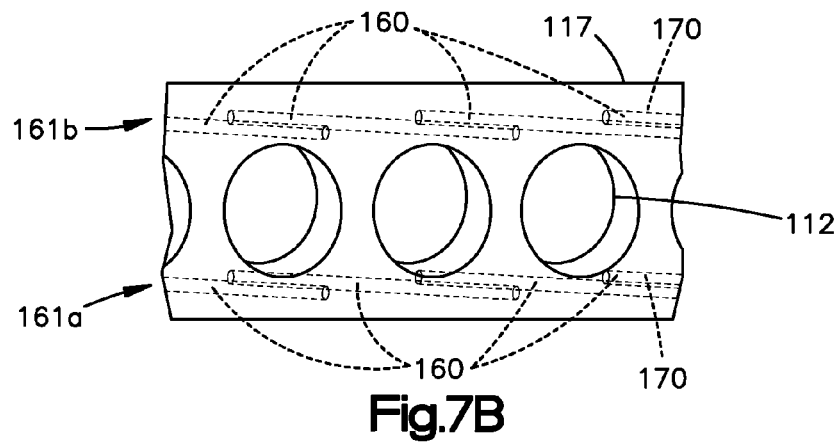
FIG. 7B is a perspective view of a radiographic image of a portion of the aiming arm illustrated in FIG. 7A, but showing the radio-opaque alignment markers in another misaligned configuration.
Figure 7C:
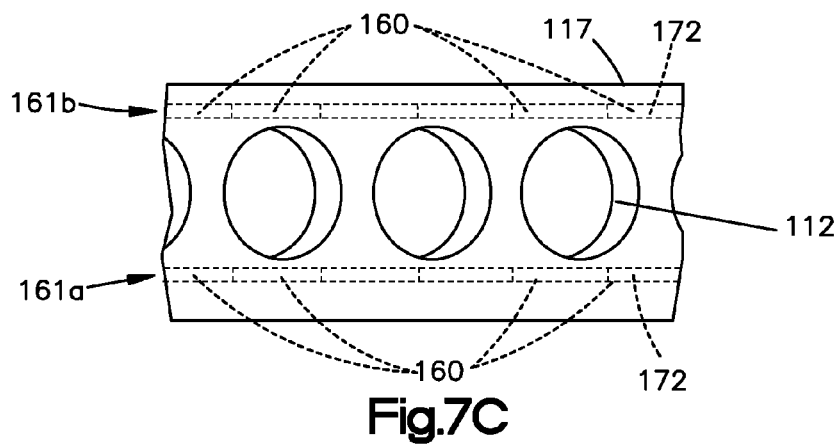
FIG. 7C is a perspective view of a radiographic image of a portion of the aiming arm illustrated in FIG. 7B, showing the radio-opaque alignment markers in an aligned configuration.

Accordingly, when an initial radiographic image produces a jagged line 170 illustrated in FIGS. 7A-B and 8A-B, the position of the radiographic image source can by moved toward or away from the aiming arm 106 along the select direction S. For instance, movement of the radiographic image source away from the aiming arm 106 can bring the radiographic image source further out of alignment with the central axes 119, while movement of the radiographic image source toward the aiming arm 106 can bring the radiographic image source into alignment with the central axes 119. If the jagged line 170 becomes more jagged, the user can conclude the that radiographic image source was moved away from alignment with the central axes 119, and the radiographic image source can then be moved in an opposite direction toward alignment with the central axes 119 until the radio-opaque markers define a line 172, which can be a linear line as illustrated in FIG. 7C. Thus, it should be appreciated that the aiming arm 106 can include at least a pair of radio-opaque markers 160 that define a first radiographic image characteristic with respect to each other when the radiographic image source is not in a desired alignment with respect to the aiming arm 106, and a second radiographic image characteristic with respect to each other when the radiographic image source is in the desired alignment with respect to the aiming arm 106. For instance, the radiographic image characteristic with respect to each other can be a distance between the radiographic members, an amount of overlap between the radiographic members, the shape of a line defined by the radiographic markers 160, or any suitable alternative radiographic image characteristic with respect to each other. Accordingly, at least a pair of the radio-opaque markers 160 of each of the respective rows 161a and 161b are aligned with respect to a first respective location, and are offset (for instance along the select direction S) with respect to a second respective location that is spaced (for instance along the select direction S) with respect to the first respective location.

In accordance with another embodiment, the radiographic image of the radio-opaque markers, such as the jagged line 170, can indicate a desired direction of movement of the radiographic image source that brings the radiographic image source into alignment with the aiming arm 106. For instance, adjacent radio-opaque markers 160 along a given row can be stacked on top of each other and sloped, such that movement of the radiographic image source along the select direction as indicated by the slope of the radio-opaque markers brings the radiographic image source into alignment with the central axes 119 of the apertures 112. It is appreciated that even though the radiographic image source is aligned with the radiographic markers 160 along the select direction S, the radiographic image source can be offset with respect to the central axes 119 of the apertures 112 along the major direction M, as illustrated in FIG. 7C.

Figure 8A:
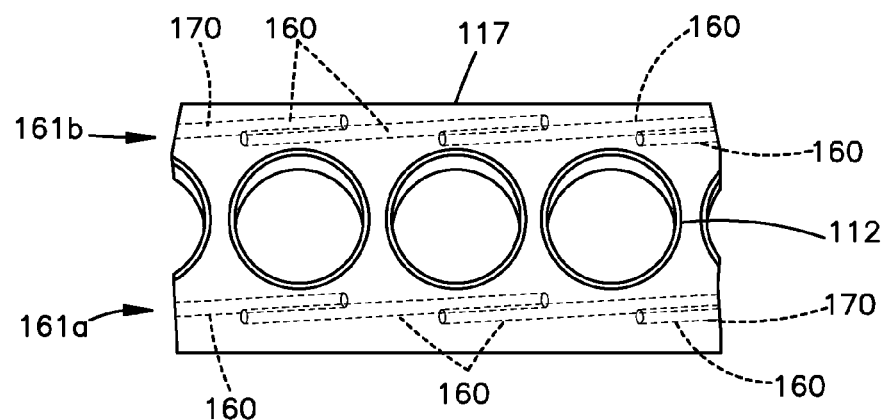
FIG. 8A is a perspective view of a radiographic image of a portion of the aiming arm illustrated in FIG. 6C as taken from a radiographic image source, showing the radio-opaque alignment markers in the misaligned configuration shown in FIG. 7A, and showing the apertures of the aiming arm in an aligned configuration along the major axis of the aiming arm.
Figure 8B:
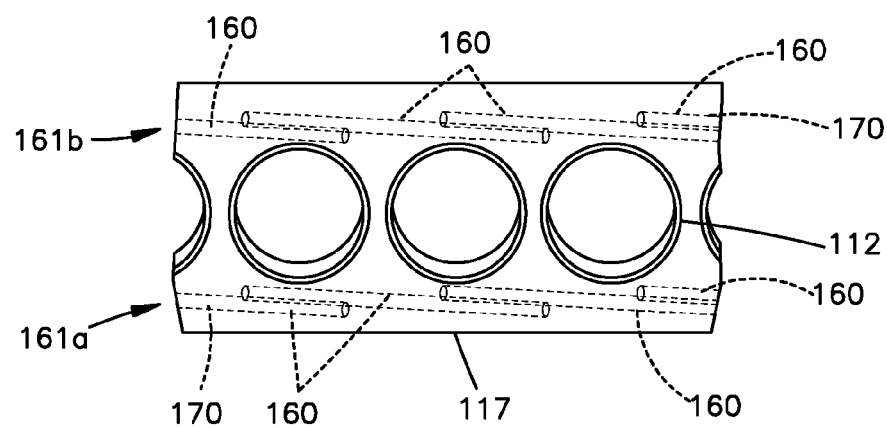
FIG. 8B is a perspective view of a radiographic image of a portion of the aiming arm illustrated in FIG. 8A, but showing the radio-opaque alignment markers in another misaligned configuration shown in FIG. 7B.

Similarly, it should be further appreciated that the radiographic image source can be aligned with the central axes 119 along the major direction M, but offset from the central axes 119 along the select direction S, as illustrated in FIGS. 8A-B. Thus, when the radio-opaque markers are aligned with each other, such that the radiographic image source is the aligned position with respect to the aiming arm 106 along the select direction S, the radiographic image source can be offset with respect to, or aligned with, the central axes of the apertures 112, for instance along the major direction M. When the radiographic image source is offset with respect to the central axes of the apertures, the apertures 112 are shaped differently than the shape that appears from a view that is aligned with the central axes of the apertures 112. For instance, the apertures 112 do not appear circular on the radiographic image when the radiographic image source is offset with respect to the central axes 119 of the apertures 112 along the major direction M, for instance along the major axis 140. Furthermore, when the radiographic image source is offset along the major direction M, the underlying apertures 604 of the intramedullary nail 602 (see FIG. 2) do not appear on the radiographic image to be aligned with the central axes 119 of the respective apertures 112. The radiographic image source can thus be adjusted in one of two directions relative to the aiming arm 106 along the major axis 140 (and thus substantially perpendicular to the select direction S) while maintaining the substantially straight line 172 as defined by the radio-opaque markers 160, which indicates that the radiographic image source is aligned with the axes 119 along the select direction S. In a first direction along the major axis 140, the radiographic image of the apertures 112 deviate further from the actual shape of the apertures 112. In a second direction opposite the first direction along the major axis 140, the radiographic image of the apertures 112 more closely approximate the actual shape of the apertures 112 until the radiographic image source is aligned along both the select direction S and the major axis 140 with respect to the central axes 119 of the apertures 112, in which case the radiographic image of the apertures 112 is substantially the same as the actual shape of the apertures 112.

Figure 8C:
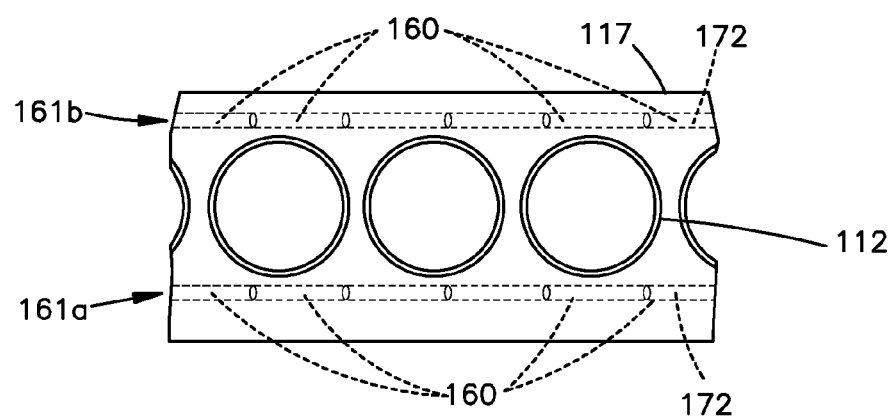
FIG. 8C is a perspective view of a radiographic image of a portion of the aiming arm illustrated in FIG. 8A, but showing the radio-opaque alignment markers in an aligned configuration as shown in FIG. 7C, and further showing the apertures of the aiming arm in the aligned configuration along the major axis of the aiming arm.

Once the radiographic image source is aligned with the aiming arm 106 along the select direction S and the major direction M, as illustrated in FIG. 8C, visual inspection of the position of the intramedullary nail 602 relative to the aiming arm 106 can determine whether the aiming arm 106 and the intramedullary nail 602 are properly aligned, and in particular whether the central axes 119 of the apertures 112 are aligned with the respective central axes of the select apertures 604 of the intramedullary nail 602. If the central axes 119 of the apertures 112 are aligned with the respective central axes of the select apertures 604 of the intramedullary nail 602, a fastener member introduced through one of the select apertures 112 will also extend through an aligned one of the apertures 604 of the intramedullary nail 602. Thus, a predetermined spatial relationship between the at least one aperture 112 and the aiming arm 106 provides an indication of whether the intramedullary nail 162 is aligned with the aiming arm 106. For instance, if the intramedullary nail 602 is substantially equidistantly spaced between, and substantially parallel to, the rows 161a and 161b of radio-opaque markers 160 of the aiming arm 106, it can be concluded that the apertures 112 of the aiming arm 106 and the apertures 604 of the intramedullary nail 602 are operatively aligned along the guide path 150 (FIGS. 2-5). If, on the other hand, the intramedullary nail 602 is not substantially equidistantly spaced from or not substantially parallel to the radio-opaque markers 160 of the aiming arm 106 when the radiographic image source is aligned with the aiming arm axes 119 of the apertures 112, then the aiming arm 106 can be deflected in the manner described above until the select apertures 112 and the apertures 604 are aligned.

In this regard, it should be appreciated that the aiming arm 106 can include at least one radio-opaque material configured in accordance with any desired embodiment that has a first configuration, such as a shape, when viewed from an undesired angle (such as oblique to the central axes of the apertures 112) and a second configuration, such as a second shape, when viewed from a desired angle (such as substantially parallel to the central axes of the apertures 112). While the radiographic markers have been described in combination with the aiming arm 106 that is attached to the base 100 of an aiming device 98, such that a spring 104 is disposed at an interface between the base portion and the aiming arm 106, it should be appreciated that the aiming arm 106 can be alternatively configured in any manner as desired. For instance, the aiming arm 106 can be attached to the base 100 in any manner desired, or can be free from the base 100 altogether. Furthermore, while the radio-opaque markers 160 have been described in combination with alignment of an aiming arm to an intramedullary nail, it should be appreciated that the radio-opaque markers can be positioned as described herein on any suitable aiming device that is to be aligned with any implant that has been implanted such that visual alignment becomes impractical.

Referring now to FIGS. 9A-9C, the radio-opaque markers 160 of each of the rows 161a and 161b can be arranged as at least one first marker 160a, such as a plurality of first markers 160a, and at least one second marker 160b, such as a plurality of second markers 160b. The first and second pluralities of markers 160a and 160b are alternatingly arranged along each of the respective rows 161a and 161b. Each of the first plurality of markers 160a and 160b of the respective first and second rows 161a and 161b can extend substantially parallel to the major direction M, or perpendicular to the central axes 119 of the apertures 112. Alternatively, each of the first and second markers 160a-b of each of the first and second rows 161a and 161b can be angularly offset with respect to both the major axis 140 and the central axes 119 of the apertures 112 as illustrated in FIGS. 7-8. Alternatively still, some of the apertures of each of the first and second rows can extend substantially parallel to the major direction M, or perpendicular to the central axes 119 of the apertures 112, and some of the radio-opaque markers 160 of each of the first and second rows 161a and 161b can be angularly offset with respect to both the major axis 140 and the central axes 119 of the apertures 112.

Each of the first plurality of markers 160a are spaced from each of the second plurality of markers 160b along the transverse direction T, or substantially parallel to the central axis 119 of the apertures 112, which can be perpendicular with respect to the major direction M. For instance, as described above, each of the first and second markers 160a-b of the first row 161a can be arranged in the second plane P2, and each of the first and second markers 160a-b of the second row 161b can be arranged in the third plane P3. Furthermore, as described above with respect to the radio-opaque markers as arranged in FIGS. 6A-8C, at least a pair of the radio-opaque markers 160 of the second plane P2 (such as a first radio-opaque marker 160a and an adjacent second radio-opaque marker 160b of the second plane P2) define a location, which can be a point on the respective markers, such that the locations are offset from each other along an axis 141, which is illustrated as a transverse axis, that is substantially parallel to the central axes 119 of the apertures 112 (and can further be coincident with the central axis 119, depending on the location of the second plane P2), or substantially perpendicular to the major direction M. Similarly, the radio-opaque markers 160 of at least a pair of the radio-opaque markers 160 of the third plane P3 (such as a first radio-opaque marker 160a and an adjacent second radio-opaque marker 160b of the third plane P3) define respective a location, such as a point, whereby that the locations are spaced offset each other along the axis 141 or substantially perpendicular to the major axis 140.

In accordance with the embodiment illustrated in FIGS. 9A-C, an entirety of one of the radio-opaque markers of the first row 161a or the second plane P2 can be offset with respect to an entirety of another one (such as an adjacent one) of the radio-opaque markers of the first row 161a (or the second plane P2) along the axis 141. Accordingly, a straight line extending along the transverse direction T (or parallel to the axis 141) that intersects one of the first or second markers 160a-b of the first row 161a does not intersect any other first or second marker of the first row 161a. Furthermore, an entirety of one of the radio-opaque markers of the second row 161b or the third plane P3 can be offset with respect to an entirety of another one (such as an adjacent one) of the radio-opaque markers of the second row 161b or the third plane P3 along the axis 141. Accordingly, a straight line extending along the transverse direction T (or parallel to the axis 141) that intersects one of the first or second markers 160a, 160b of the second row 161b does not intersect any other first or second marker of the of the second row 161b. Accordingly, it can be said that at least a portion of a first radio-opaque markers 160a of a respective plane P1 or P2 can be offset with respect to at least a portion of a second radio-opaque marker of the respective plane along both the axis 141 and the major direction M.

Accordingly, when a radiographic image source is positioned at a first position, for instance, aligned with at least one of the radio-opaque markers 160 along a first direction, which can be angularly offset with respect to the central axes 119, the markers 160 of each row 161a and 161b can define the nonlinear or jagged line 170. When a radiographic image source is positioned at a first position, for instance, aligned with at least one of the radio-opaque markers 160 along a first direction, which can be angularly offset with respect to the central axes 119, the markers 160 of each row 161a and 161b can define the linear straight line 172.

The elongate arm may 106 include a marker 160 or markers of a radio-opaque material. The radio-opaque material is suitably present in the distal portion 110 of the aiming arm 106, and may be present near to the apertures 112. The radio-opaque markers 160 can be visible in a radiographic image (for instance, during real-time radiography) so as to assist in visual alignment of the aiming arm 106, including the apertures 112, with complementary apertures on an intramedullary nail or other fixation member while adjusting the opposed members 114 and 116 so as to correspondingly adjust the position the apertures 112 to place the apertures 112 in register with the complementary apertures.

The radio-opaque markers 160 may be configured as a wire, a plate, dots, spheres, or any suitable alternatively constructed members. The radio-opaque markers 160 may be present at the edge or border of the aiming arm 106 or other predetermined location so as to allow the use to determine the position of the edge of the aiming arm 106 relative to the intramedullary nail. The radio-opaque markers 160 may also be positioned so as to delineate the position(s) of one or more apertures 112 to allow the user to place the apertures 112 in register with complementary apertures or other features of an intramedullary nail or other fixation member. The radio-opaque markers 160 can be oriented substantially parallel to the major axis 140.

Referring now to FIGS. 10A-C, the aiming arm 106 can include at least two radio-opaque wires 163, such as four radio-opaque wires 163 that can be arranged in pairs and elongate along the major direction M. The wires 163 can define a dimension that is substantially equal in both the select direction S and the transverse direction T. At least one wire 163, such as a first pair 163*a* of the wires 163, can be disposed on a first side of the apertures 112 with respect to the select direction S, and a second at least one wire 163, such as a second pair 163*b* of the wires 163, can be disposed on a second side of the apertures 112 with respect to the select direction S opposite the first side. The pairs 163*a-b* of wires 163 can be equidistantly spaced from the major axis 140 as desired. Each of the wires 163 can be elongate and continuous along the major direction M. and can span at least a pair of the apertures 112, such as a majority of the apertures 112. First and second wires 163 of each of the pairs 163*a-b* of wires can be spaced along the transverse direction T, and spaced equidistantly from the major axis 140 along the select direction S.

As illustrated in FIG. 10B, the aiming arm 106 includes radio-opaque markers 160 that are present in the form of a pair of plates 165. The plates 165 can define a dimension in the select direction S and the transverse direction T, such that the dimension in the transverse direction T is greater than the dimension in the select direction S. A first one of the plates 165 can be disposed on a first side of the apertures 112 with respect to the select direction S, and a second one of the plates 165 can be disposed on a second side of the apertures 112 with respect to the select direction S opposite the first side. The plates 165 can be equidistantly spaced from the major axis 140 as desired. Each of the plates 165 can be elongate and continuous along the major direction M. and can span at least a pair of the apertures 112, such as a majority of the apertures 112.

As illustrated in FIG. 10C, the aiming arm 106 includes radio-opaque markers 160 that are present in the form of a pair of wires 163 and a plate 165 that can be disposed on opposite sides of the apertures 112 with respect to the select direction S, and can be equidistantly spaced from the apertures 112 along the select direction S. The radio-opaque markers 160, including the wires 163 and the plates 165, can be in the form of radio-opaque paint, inserts that are inserted into the body of the aiming arm 106, or the like. It should be further appreciated that the nail 602 can be made of a radio-opaque material or include radio-opaque markers. It should be appreciated that the radio-opaque markers 160 illustrated in FIGS. 10A-C positioned on opposite sides of the apertures 112, and thus on opposite sides of the major axis 140, are disposed in respective second and third planes P2 and P3 that are positioned on opposite sides with respect to the first plane P1 defined by the major axis 140 of the aiming arm 106 and the central axes of the apertures 112, as illustrated in FIGS. 5 and 6C. Further, it should be appreciated that the wires 163 and plates 165 are elongate along a direction that includes a directional component that includes the major direction M, and the plates 165 can be further elongate along a direction that includes a directional component that includes the transverse direction T.

Figure 11:
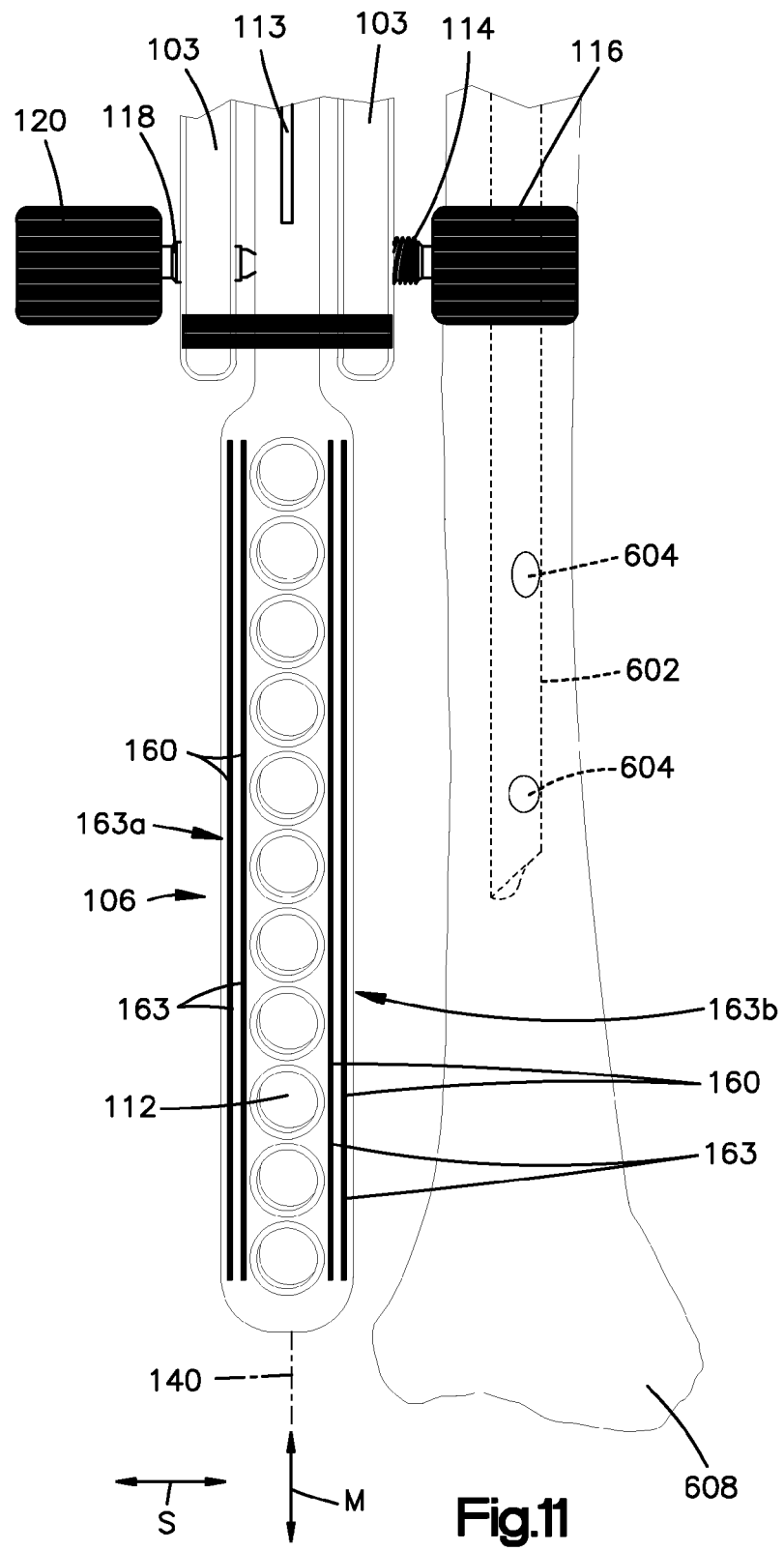
FIG. 11 is an enlarged radiographic image of the implantation assembly as illustrated in FIG. 10A.
Figure 12:
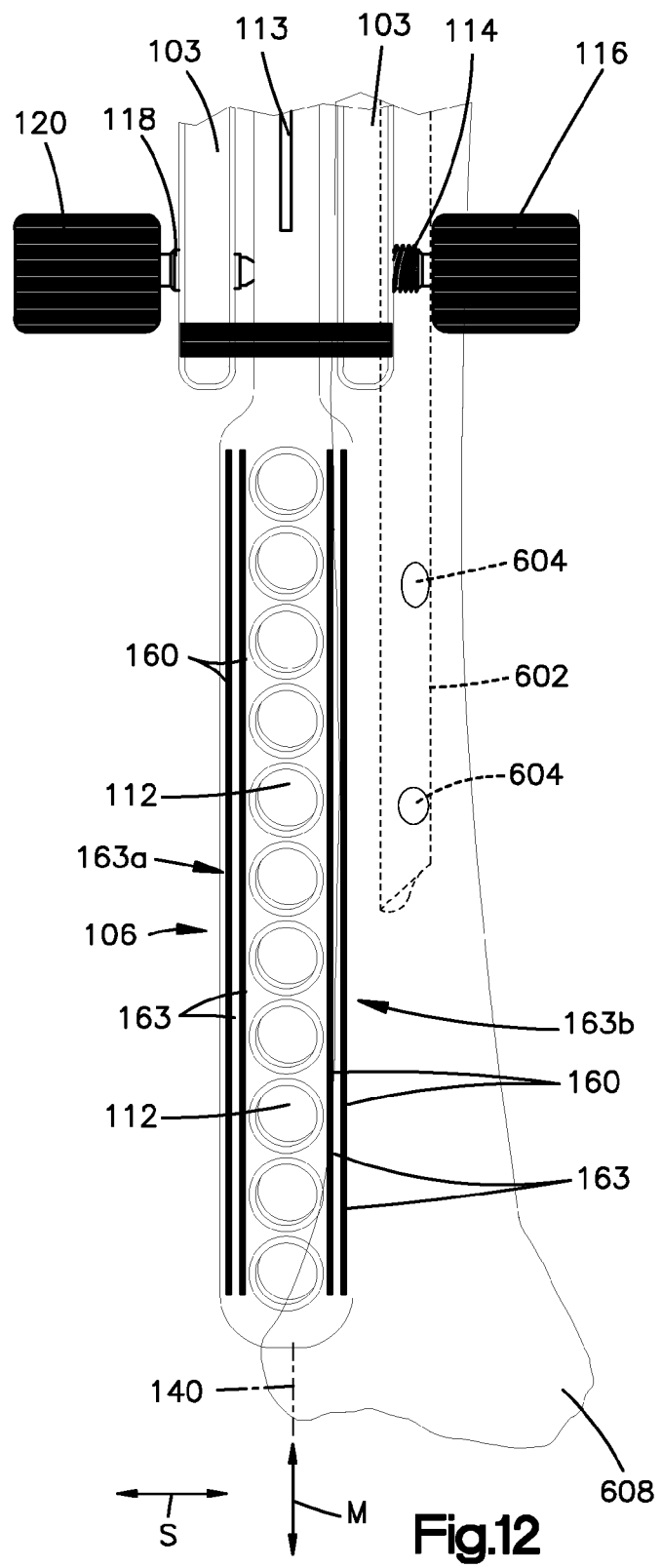
FIG. 12 is another radiographic image of the implantation assembly as illustrated in FIG. 11.
Figure 13:
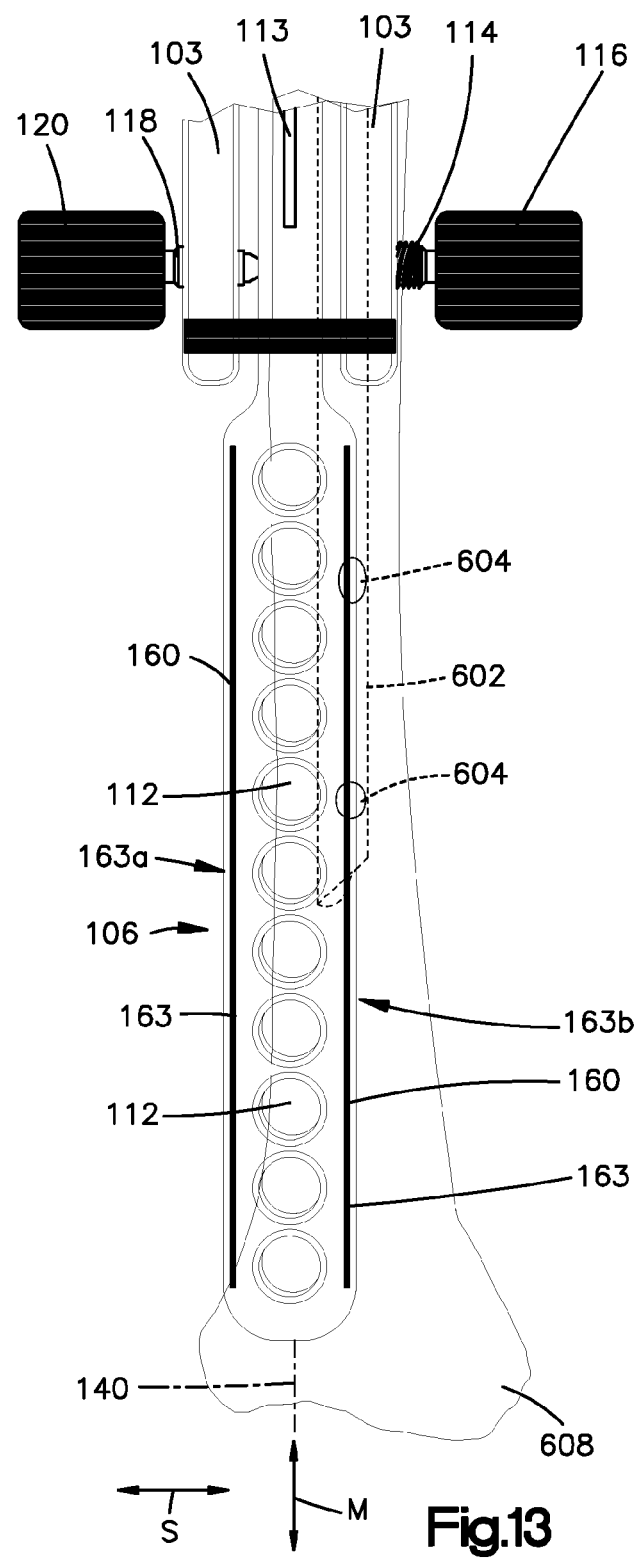
FIG. 13 is a radiographic image of an implantation assembly as illustrated in FIG. 10A, but showing the aiming arm including a radio-opaque material in accordance with another embodiment.

Referring now to FIGS. 11-12, the aiming device 98 includes radio-opaque markers 160 present in the form of four wires 163 that can be arranged in two pairs of wires carried by the aiming arm 106 in the manner described above with respect to FIG. 10A. An intramedullary nail 602 that has been installed into a bone 608 is also visible in the radiographic image. The wires 163 of the radiographic image can be inspected to determine whether each wire 163 of a given pair 163*a-b* of wires is overlapped with respect to the other wire 163 of the given pair. If the wires 163 of each of the pairs 163*a-b* are not overlapped, as illustrated in FIGS. 11 and 12, then it can be concluded that the radiographic image is in a first position that does not reflect a desired view of the aiming arm 106 and nail 602, and alignment between the aiming arm 106 and the nail 602 can not be reliably determined. Once the position of the radiographic image source has been corrected to a second position different than the first position such that each wire 163 of the pairs 163*a-b* of wires overlap as illustrated in FIG. 13, it can be concluded that the second position of the radiographic image is a desired position that reflects the desired view of the aiming arm 106 and nail 602. For instance, the desired view can be along a direction substantially parallel to the central axes of the apertures 112 of the aiming arm 106.

Figure 14:
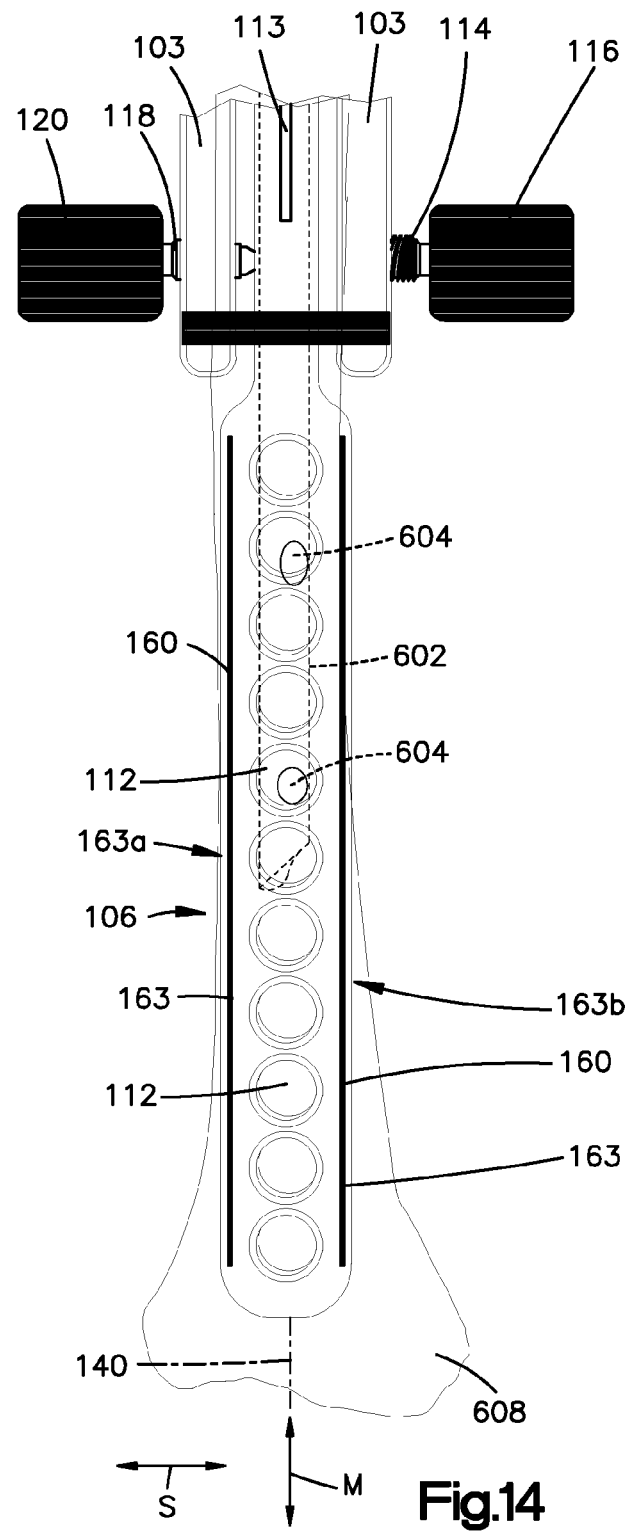
FIG. 14 is another radiographic image of an implantation assembly as illustrated in FIG. 13.
Figure 15:
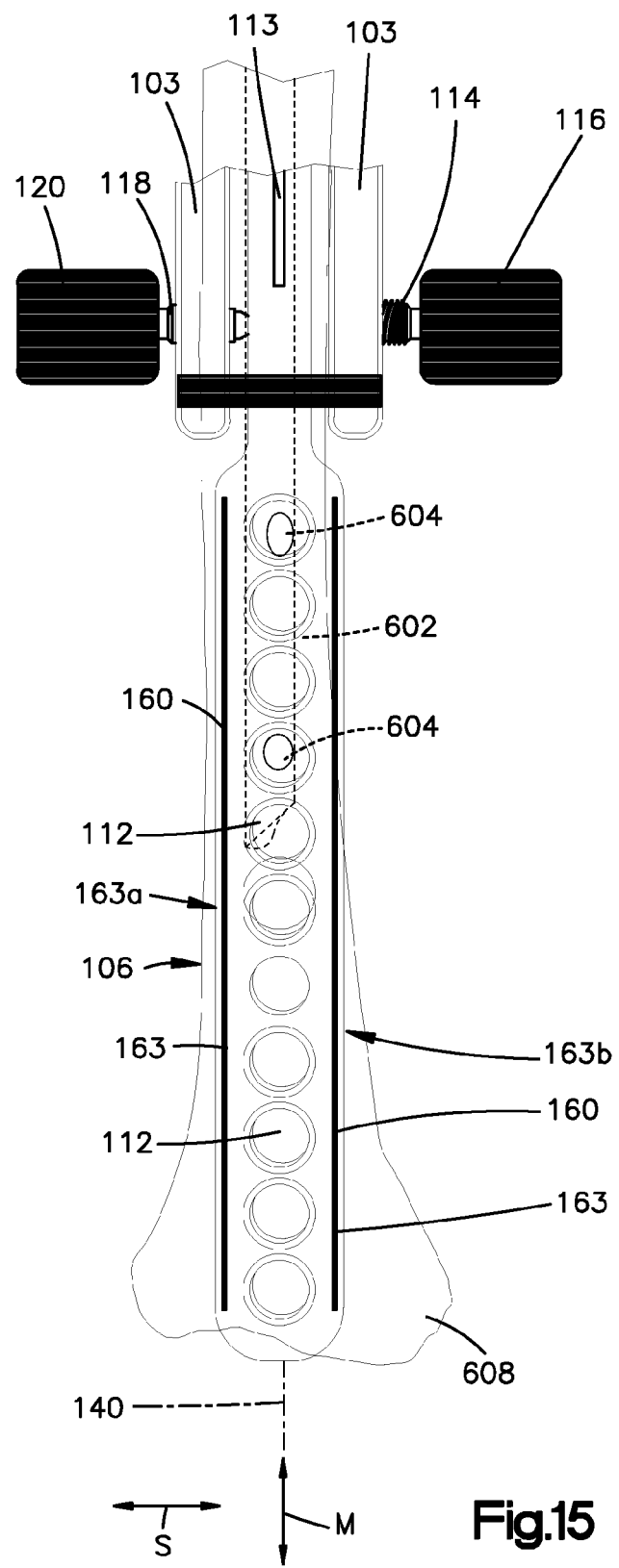
FIG. 15 is another radiographic image of an implantation assembly as illustrated in FIG. 14.

Once the desired view is established, visual inspection of the position of the nail 602 relative to the arm can determine whether the aiming arm 106 and the nail 602 are properly aligned. For instance, if the intramedullary nail 602 is substantially equidistantly spaced between, and substantially parallel to, the radio-opaque wires of the aiming arm 106, it can be concluded that the apertures 112 of the aiming arm 106 and the apertures 604 of the nail 602 are operatively aligned as illustrated in FIG. 15. If, on the other hand, the nail 602 is not substantially equidistantly spaced from and substantially parallel to the radio-opaque wires of the aiming arm 106 as illustrated in FIG. 14, the aiming arm 106 can be deflected in the manner described above until the nail 602 and the aiming arm 106 are aligned as desired, such that the apertures 112 and 604 substantially coincide. Screws or alternatively constructed bone anchors can then be driven through the apertures 144 of the mask 142 and the apertures 112 of the aiming arm 106, and into the corresponding aligned apertures 604 of the nail 602. Thus, the radio-opaque markers 160 in the form of wires 163 can define a first image characteristic with respect to each other in the form of less than an entire overlap of at least one of the wires with respect to another of the wires, wires of a pair of wires that are spaced along the transverse direction T, which is substantially perpendicular to the major direction M and the select direction S, and a second radiographic image characteristic with respect to each other, such as an entire overlap of at least one of the wires with respect to another of the wires, when the radiographic image source is in the desired alignment with respect to the aiming arm 106.

Figure 16:
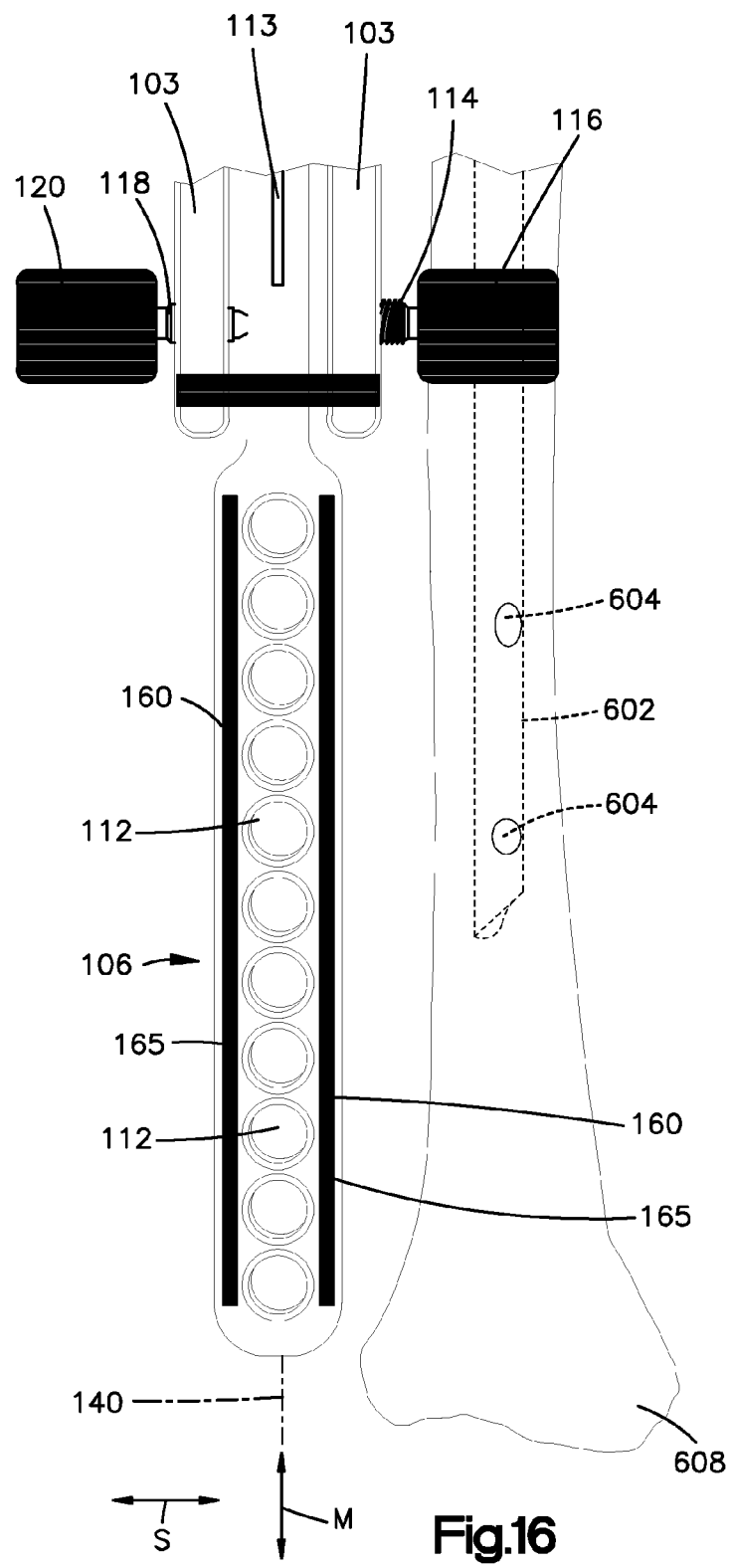
FIG. 16 is an enlarged radiographic image of the implantation assembly as illustrated in FIG. 10B.

Referring to FIG. 16, the aiming device 98 can include radio-opaque markers 160 in the form of two plates 165 that are carried by the aiming arm 106 at a location on opposed sides of the apertures 112 with respect to the select direction, as described above with respect to FIG. 10B. Thus, the radiographic image can be taken from a first position whereby the imaged thickness of the plates 165 along the select direction S has a first size, which can be less than or greater than the desired size so as to indicate that the first position is not in a desired position. The radiographic image can be moved to a second position different than the first position until the thickness of the plates along the select direction S has a second size that is substantially equal to a desired size. In one example, each of the plates 165 can be dimensioned greater in the transverse direction T than in the select direction S, such that the desired imaged size of the thickness of the plates 165 along the select direction S can be a minimal thickness, equal to the actual thickness of the plates 165 along the select direction S. Alternatively, each of the plates 165 can be oriented in the body of the aiming arm 106 such that the plates 165 can be dimensioned greater in the transverse direction S than in the transverse direction T, such that the desired imaged size of the thickness of the plates 165 along the select direction S can be a maximum thickness, equal to the actual thickness of the plates 165 along the select direction S. Once the imaged size of the thickness of each of the plates 165 is substantially equal to the desired imaged size, for instance minimized or maximized, the aiming arm 106 can be positioned such that the nail 602 is positioned substantially equidistantly between and substantially parallel to the plates 165, such that the bone anchors can be driven through the apertures 112 of the aiming arm 106 into the apertures 604 of the nail 602. Thus, the radio-opaque markers 160 in the form of plates 165 can define a first image characteristic in the form of a thickness (such as a greater than a minimum thickness or less than a maximum thickness) of the plates 165 along the select direction S when the radiographic image source is in a first position with respect to the aiming arm 106, and a second radiographic image characteristic, such as a minimum thickness or a maximum thickness along the select direction S, when the radiographic image source is in a second desired position with respect to the aiming arm 106 that is different than the first position and in a desired alignment with respect to the aiming arm 106.

Figure 17:
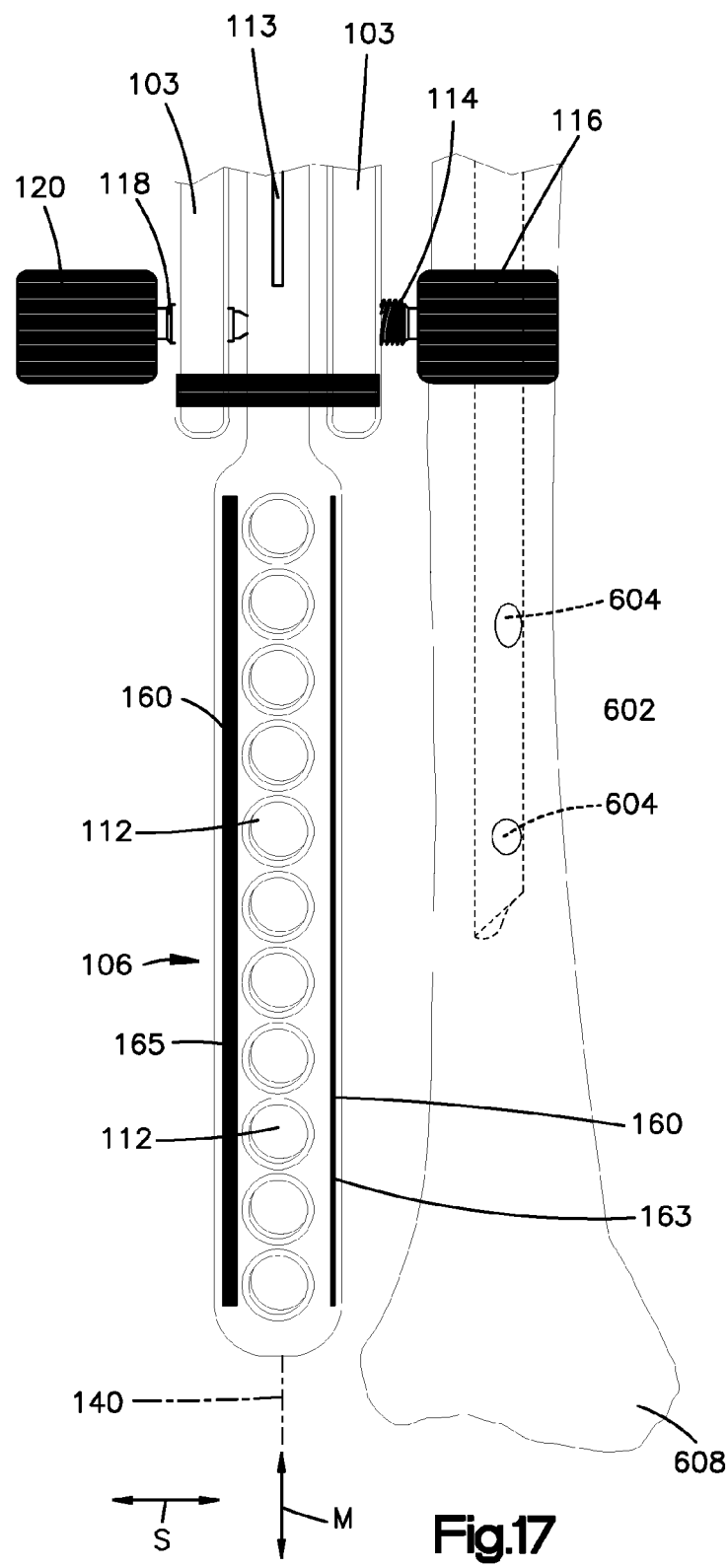
FIG. 17 is an enlarged radiographic image of the implantation assembly as illustrated in FIG. 10C.

Referring now to FIG. 17, the aiming device 98 includes radio-opaque markers 160 present as a pair of wires 163 and a plate 165 that are carried by the aiming arm 106 at a location non opposed sides of the apertures 112, as illustrated in FIG. 10C. Thus, the radiographic image can be taken from a firs position whereby the thickness of the plate has a size that can be greater than or less than desired as described above with respect to the plates 165 in FIG. 10B. The radiographic image can be repositioned to a second position, whereby the imaged size of the thickness of the plate 165 along the select direction S is desired, such as a minimized or maximized thickness, and the aiming arm 106 can be positioned such that the nail 602 is positioned substantially equidistantly between and substantially parallel to the wire 163 and the plate 165, such that the bone anchors can be driven through the apertures 112 of the aiming arm 106 into the apertures 604 of the nail 602. Thus, it should be appreciated that the aiming device 98 can include at least one radio-opaque material configured in accordance with any desired embodiment that has a first configuration, such as a shape, when viewed from an undesired angle (such as oblique to the central axes of the apertures 112) and a second configuration, such as a second shape, when viewed from a desired angle (such as substantially parallel to the central axes of the apertures 112).

The foregoing description is illustrative only and does not limit the scope of the present disclosure. Embodiments not described above may nonetheless be within the scope of the appended claims.

What is claimed:

1. An aiming arm configured to be aligned with an implant, the aiming arm comprising:
   a body defining at least one aperture, the aperture defining a central axis that extends along a first plane, the central axis intersecting a major axis of the body that lies in the first plane, the body defining at least first and second straight linear radio-opaque markers,
   wherein the first and second straight linear radio-opaque markers extend in a second plane and are spaced from each other along the second plane, the second plane being parallel to the first plane, and each of the first and second straight linear radio-opaque markers defines a respective location, such that the location of the first straight linear radio-opaque marker is offset with respect to the location of the second straight linear radio-opaque marker along both a direction that is substantially parallel to the central axis of the at least one aperture, and a direction that is parallel to the major axis,
   wherein when a radiographic image is taken of the aiming arm from a first viewpoint such that the aiming arm is aligned with a source of the radiographic image, the first and second straight linear radio-opaque markers combine to define an unbroken substantially straight line, and when a radiographic image is taken of the aiming arm from a second viewpoint different from the first viewpoint, the first and second straight linear radio-opaque markers combine to define a jagged line.

2. The aiming arm as recited in claim 1, further comprising third and fourth radio-opaque markers that extend in a third plane and are spaced from each other along the third plane, the third plane parallel to the second plane, and each of the third and fourth radio-opaque markers defines a respective location, such that the location of the third radio-opaque marker is offset with respect to the location of the fourth radio-opaque marker along a direction that is substantially parallel to the central axis of the at least one aperture.

3. The aiming arm as recited in claim 1, wherein the first and second radio-opaque markers are elongate in a direction parallel to the major axis.

4. The aiming arm as recited in claim 1, wherein the first and second radio-opaque markers are elongate in a direction angularly offset with respect to the major axis.

5. The aiming arm as recited in claim 1, wherein at least one of the radio-opaque markers is elongate along a direction substantially parallel to the major axis and at least one of the radio-opaque markers is elongate along a direction that is angularly offset with respect to the major axis.

6. The aiming arm as recited in claim 1, wherein the first and second radio-opaque markers are discontinuous with respect to each other.

7. The aiming arm as recited in claim 1, wherein the first and second radio-opaque markers are continuous.

8. The aiming arm as recited in claim 2, wherein the second and third planes are equidistantly spaced with respect to the first plane.

9. The aiming arm as recited in claim 1, wherein an entirety of the first radio-opaque marker is offset with an entirety of the second radio-opaque marker along the direction that is substantially parallel to the central axis of the at least one aperture.

10. The aiming arm as recited in claim 1, wherein the first and second radio-opaque markers are disposed on one side of the major axis along a select direction that is substantially perpendicular to the major axis.

11. The aiming arm as recited in claim 10, wherein the first and second radio-opaque markers define a first pair of radio-opaque markers, and the body defines a second pair of radio-opaque markers that are positioned on an opposite side of the major axis with respect to the first pair of radio-opaque markers.

12. The aiming arm as recited in claim 1, wherein the radio-opaque markers comprise wires.

13. A bone fixation system comprising:
   an aiming arm that defines at least one aperture on a major axis of the aiming arm, the major axis extending along a major direction, the aiming arm carrying a plurality of linear markers, the plurality of linear markers comprising at least a pair of radio-opaque markers that are elongate along a direction that includes a directional component that includes the major direction, each of the pair of radio-opaque markers defining a gap therebetween, such that 1) when a radiographic image is taken of the aiming arm from a first viewpoint while the aiming arm is not aligned with a source of the radiographic image, no others of the plurality of linear markers cooperates with the pair of radio-opaque markers to define a single unbroken substantially straight line that extends across the gap and 2) when a radiographic image is taken of the aiming arm from a second viewpoint different from the first viewpoint such that the aiming arm is aligned with the source of the radiographic image, a radio-opaque marker of the plurality of linear markers is disposed in the gap and cooperates with the pair of radio-opaque markers to define the singular unbroken substantially straight line across the gap.

14. The bone fixation system as recited in claim 13, further comprising an implant that defines at least one aperture, wherein a predetermined spatial relationship between the at least one aperture and the aiming arm provides an indication of whether the implant is aligned with the aiming arm.

15. The bone fixation system as recited in claim 13, wherein the first radiographic image characteristic comprises a shape of at least one line defined by the radio-opaque markers.

16. The bone fixation system as recited in claim 13, wherein the first radiographic image characteristic is a jagged line.

17. The bone fixation system as recited in claim 13, wherein the radio-opaque markers are arranged in first and second rows, such that the at least one aperture is disposed between the first and second rows.

18. The bone fixation system as recited in claim 13, wherein the first radiographic image characteristic indicates a desired direction along which to move the source of the radiographic image relative to the aiming arm so as to bring the source of the radiographic image into alignment with the aiming arm.

19. The bone fixation system as recited in claim 18, wherein the radio-opaque markers are stacked along the desired direction on the radiographic image.

* * * * *